(12) United States Patent
Zhou et al.

(10) Patent No.: US 9,421,514 B2
(45) Date of Patent: Aug. 23, 2016

(54) POROUS MATERIALS CONTAINING BUILT-IN SINGLE MOLECULE TRAPS FOR SMALL MOLECULE CAPTURE

(75) Inventors: Hong-Cai Zhou, College Station, TX (US); Mario Wriedt, College Station, TX (US); Julian Sculley, College Station, TX (US); Jian-Rong Li, College Station, TX (US)

(73) Assignee: Texas A&M University System, College Station, TX (US)

( * ) Notice: Subject to any disclaimer, the term of this patent is extended or adjusted under 35 U.S.C. 154(b) by 206 days.

(21) Appl. No.: 14/342,530

(22) PCT Filed: Jun. 25, 2012

(86) PCT No.: PCT/EP2012/062262
§ 371 (c)(1),
(2), (4) Date: Aug. 8, 2014

(87) PCT Pub. No.: WO2013/029830
PCT Pub. Date: Mar. 7, 2013

(65) Prior Publication Data
US 2015/0071845 A1    Mar. 12, 2015

Related U.S. Application Data

(60) Provisional application No. 61/530,772, filed on Sep. 2, 2011.

(51) Int. Cl.
*B01D 53/02* (2006.01)
*B01J 20/22* (2006.01)
*C01B 3/00* (2006.01)
(Continued)

(52) U.S. Cl.
CPC ............. *B01J 20/226* (2013.01); *B01D 53/02* (2013.01); *B01J 20/2809* (2013.01); *B01J 20/28066* (2013.01); *C01B 3/0015* (2013.01); *C01B 31/20* (2013.01); *C07F 1/08* (2013.01); *C07F 11/005* (2013.01); *C07F 15/0046* (2013.01); *C07F 15/0053* (2013.01); *B01D 2253/204* (2013.01); *B01D 2253/308* (2013.01); *B01D 2257/102* (2013.01); *B01D 2257/104* (2013.01); *B01D 2257/108* (2013.01); *B01D 2257/30* (2013.01); *B01D 2257/40* (2013.01); *B01D 2257/50* (2013.01); *B01D 2257/504* (2013.01);
(Continued)

(58) Field of Classification Search
USPC .............................................. 95/90, 139, 900
See application file for complete search history.

(56) References Cited

U.S. PATENT DOCUMENTS

2003/0004364 A1* 1/2003 Yaghi .................... B01J 20/226
556/46
2008/0184881 A1* 8/2008 Zhou ..................... B01J 20/226
95/43

(Continued)

OTHER PUBLICATIONS

Charlane C. Correa et al., "Transition metal complexes with squarate anion and the pyridyl-donor ligand 1,3-bis (4-pyridyl)propane (BPP); Synthesis, crystal structure and spectroscopic investigation," Polyhedron, vol. 26, 2007, pp. 989-995.

(Continued)

*Primary Examiner* — Frank Lawrence
(74) *Attorney, Agent, or Firm* — Reising Ethington P.C.

(57) ABSTRACT

Provided herein are porous single-molecule trap materials with fixed pore sizes that are capable of trapping one molecule per cavity.

15 Claims, 21 Drawing Sheets

(51) Int. Cl.
  C07F 15/00    (2006.01)
  C07F 1/08     (2006.01)
  C07F 11/00    (2006.01)
  B01J 20/28    (2006.01)
  C01B 31/20    (2006.01)

(52) U.S. Cl.
  CPC ........... B01D2257/702 (2013.01); Y02C 10/08 (2013.01); Y02E 60/328 (2013.01)

(56) References Cited

U.S. PATENT DOCUMENTS

2009/0211445 A1    8/2009   Mirkin et al.
2012/0073438 A1*   3/2012   Ryan ................... B01D 53/02
                                               95/127
2013/0047849 A1*   2/2013   Zhang .................. B01D 53/02
                                               95/130

OTHER PUBLICATIONS

Zhi-Yong Fu et al., "Three Novel Polymeric Frameworks Assembled from Cd(II), Co(II), and Mn(II) with the Mixed Organic Ligands 3,4-Pyridinedicarboxylate, 1,3-Bis(4-pyridyl)propane, or 1,2-Bis(4-pyridyl)ethane," Eur. J. Inorg. Chem., 2003, pp. 2670-2677.
Stuart R. Batten et al., "Studies of the construction of coordination polymers using linear pyridyl-donor ligands," Inorganica Chimica Acta, vol. 292, 1999, pp. 231-237.
Banglin Chen et al., "Rationally Designed Micropores within a Metal-Organic Framework for Selective Sorption of Gas Molecules," Inorganic Chemistry, vol. 46, No. 4, 2007, pp. 1233-1236.
Qi-Yong Chen et al., "A 3D-diamond-like tetrazole-based Zn(II) coordination polymer; Crystal structure, nonlinear optical effect and luminescent property," Inorganic Chemistry Communications, vol. 11, No. 9, 2008, pp. 969-971.
A-Qing Wu et al., New Copper(II) and Nickle(II) Complexes with Bifunctional Tetrazolate-5-carboxylate Ligands: Synthesis, Crystal Structures, and Magnetic Properties, Aust. J. of Chem., vol. 62, No. 12, 2009, pp. 1622-1630.
Mei-Feng Wu et al., "Hydrothermal synthesis, crystal structures and luminescent properties of zinc (II) coordination polymers constructed by bifunctional tetrazolate-5-carboxylate ligands," CrystEngComm, vol. 12, 2010, pp. 260-269.
Sujoy Baitalik et al., "Spectroscopic and redox properties of Rh(III)Ru(II) and Ru(II)Ru(II) complexes derived from 2,2'-bipyridine, pyrazole-3,5-bis(benzimidazole) and 1,2,4-triazole-3,5-dicarboxylic acid as bridging ligands," Polyhedron, vol. 23, 2004, pp. 913-919.
Tapas Kumar Maji et al, "Guest-Induced Asymmetry in a Metal-Organic Porous Solid with Reversible Single-Crystal-to-Single-Crystal Structural Transformation," J. Am. Chem. Soc., vol. 127, 2005, pp. 17152-17153.
Deyuan Kong et al., "Rational Design and Synthesis of Porous Organic-Inorganic Hybrid Frameworks Constructed by 1,3,5-Benzenetriphosphonic Acid and Pyridine Synthons," Inorganic Chemistry, vol. 45, No. 3, 2006, pp. 977-986.
Xiuli Wang et al., Self-Assembly of Organic-Inorganic Hybrid Materials Constructed from Eight-Connected Coordination Polymer Hosts with Nanotube Channels and Polyoxometalate Guests as Templates, Inorganic Chemistry, vol. 47, No. 7, 2008, pp. 2442-2448.
Feng Luo et al., "One metallic-organic framework with chain-like counterions and water molecules capsulated in the 1D chiral channels from the 2D 2-fold inclined interpenetrating (4,4) nets," Journal of Molecular Structure, vol. 828, No. 1-3, 2007, pp. 162-165.
Maw-Cherng Suen et al., "Synthesis and structures of three new coordination polymers generated from the flexible 1,3-bis(4-pyridyl)propane ligand and zinc salts," Polyhedron, vol. 25, 2006, pp. 2325-2332.
Kjell Ove Kongshaug et al., "Design of Novel Bilayer Compounds of the CPO-8 Type Containing 1D Channels," Inorganic Chemistry, vol. 45, No. 6, 2006, pp. 2424-2429.
Jian Wu, "A novel porous network with interpenetrating topology," Cryst. Res. Technol., vol. 44, No. 2, 2009, pp. 221-224.
Database Caplus [Online], Chemical Abstracts Service, Columbus, Ohio, 2009 (2 pages).
Maryam Ghoreishi Amiri et al., "A Dynamic Crystal-to-Amorphous Transformation Microporous Zn(II) Mixed Neutral-ligand Metal-organic Polymer {[Zn(bpp)2(μ-4,4'-bipy)-(H2O)2](ClO4)2•H2O}n," Z. Anorg. Allg. Chem., vol. 635, 2009, pp. 1673-1677.
International Search Report for PCT/EP2012/062262; dated Dec. 4, 2012; 9 pages.

* cited by examiner

POROUS MATERIALS CONTAINING BUILT-IN SINGLE MOLECULE TRAPS FOR SMALL MOLECULE CAPTURE

STATEMENT REGARDING FEDERALLY SPONSORED RESEARCH OR DEVELOPMENT

This invention was made with government support under DE-AR0000073 awarded by the U.S. Dept. of Energy. The government has certain rights in the invention.

The present invention relates to porous metal-organic materials. In particular, the invention relates to porous metal-organic materials comprising molecular traps for the capture of single molecules, and methods of preparing same.

Increasing concern regarding the release of $CO_2$ into the atmosphere over the last decade has focused research attention on methods of mediating anthropogenic carbon dioxide emissions and increasing the efficiency of fossil fuel harvesting. In particular, $CO_2$ capture from energy generation sources and the upgrade of natural gas have been identified as key reactions for which these concerns must be addressed. However, the separation of specific molecules, such as $CO_2$ from $N_2$ and other gases in the case of $CO_2$ capture from flue gas streams, and of $CO_2$ from $CH_4$ in the case of upgrading natural gas, suffers from a number of challenges, primarily concerning the difficulties in tuning sorption reactions to the molecule of interest. Furthermore, methods such as amine scrubbing which are traditionally used in this field, suffer from drawbacks including significant power demand during sorbent regeneration.

Accordingly, there is a need for new methods of targeting molecules at the individual molecular level, which demonstrate high selectivity and low regeneration energy requirements, and which can obviate or mitigate some of the disadvantages associated with the prior art.

In a first aspect of the present invention there is provided a porous material comprising (i) a single pore having a single pore size or (ii) a plurality of pores having an average pore size, wherein the single pore size or the average pore size is proportioned to accommodate a single gas molecule to the exclusion of additional gas molecules.

Porous metal-organic materials have been prepared. Depending on whether the materials possess discrete or extended structures, the materials may be referred to as metal-organic polyhedra (MOP) or metal-organic frameworks (MOF), respectively. The pore size and cavities of the materials have been configured particularly for trapping one molecule at a time. For instance, a "single-molecule trap" (SMT) of 0.7 nm in size is described herein containing two anchors (open metal sites) for trapping one $CO_2$ molecule. The length of $CO_2$ (0.24 nm) plus twice the distance between an O atom and an open metal site (0.23×2=0.46 nm) equals 0.7 nm, which allows the two open metal sites to interact with one $CO_2$ molecule. The single molecule trap can exhibit strong interaction with the confined molecule, without the permanence of a chemical reaction. Exemplary materials with different anchor metal sites for $CO_2$ capture are described herein. The adsorption selectivity of $CO_2$ over other gases such as $N_2$, $CH_4$, $SO_2$, and $O_2$ has been evaluated both theoretically and experimentally, revealing that these single-molecule trap materials adsorb $CO_2$ exclusively. In addition, single-molecule traps for $H_2$ are also provided. Other materials containing single-molecule traps for other small molecules are also described herein. These materials may be used in applications such as small molecule capture (e.g., carbon capture), activation, conversion, storage, or for other purposes involving binding single gas molecules.

A primary technical advantage associated with this disclosure is that porous materials may be configured at the molecular level for one-to-one small gas molecule capture and separation, such as for the purposes of $H_2$ storage, $CO_2$ separation or $N_2$ activation, in a manner previously unavailable. Porous materials may be configured to trap specific small gas molecules but exclude other molecules, thereby separating them.

The porous material may be synthetic, as opposed to naturally-occurring. The single pore size or the average pore size may adopt a variety of sizes. In some embodiments, the single pore size or the average pore size ranges from about 6.6 nm in length to about 9.5 nm in length, wherein "length" refers to the longest distance in any one direction of the pore. In some embodiments, the single pore size or the average pore size ranges from about, at most about, or at least about 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, to about, at most about, or at least about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 nm in length, or higher, or any range derivable therein. In some embodiments, the single pore size or the average pore size is selected from:

(i) 6.8-7.4 nm in length, wherein the single gas molecule may be $CO_2$, for example;
(ii) 6.6-7.0 nm in length, wherein the single gas molecule may be $H_2$, for example;
(iii) 7.7-8.5 nm in length, wherein the single gas molecule may be $N_2$ or CO, for example;
(iv) 7.3-8.1 nm in length, wherein the single gas molecule may be $O_2$, for example;
(v) 7.8-8.8 nm in length, wherein the single gas molecule may be $CH_4$, for example;
(vi) 6.8-7.4 nm in length, wherein the single gas molecule may be $C_2H_4$, for example;
(vii) 8.5-9.5 nm in length, wherein the single gas molecule may be $C_3H_6$, for example;
(viii) 8.1-9.1 nm in length, wherein the single gas molecule may be $SO_2$, for example;
(ix) 7.6-8.6 nm in length, wherein the single gas molecule may be $H_2S$, for example;
(x) 8.5-9.5 nm in length, wherein the single gas molecule may be $CS_2$, for example;
(xi) 6.9-7.8 nm in length, wherein the single gas molecule may be $NH_3$, for example;
(xii) 7.5-8.5 nm in length, wherein the single gas molecule may be NO, for example.

A pore may be temperature-adjustable. A pore may not be temperature-adjustable. U.S. Pat. No. 7,789,943, incorporated herein by reference in its entirety, describes materials having pores that are temperature-adjustable. The temperature-dependent pore openings of the materials are defined by the equation: $D=D_O+\alpha T$, where D is the kinetic opening, in Angstroms, of the temperature-adjustable pore opening, $D_O$ is the temperature-adjustable pore opening at zero degrees Kelvin, $\alpha$ is a constant related to a ligand of the material, and T is the temperature in degrees K. If a porous material comprises temperature-adjustable pores, the material may be used, for example, to separate molecules of various sizes from each other. Separation may be accomplished by maintaining the material at a temperature, typically a preselected temperature, to set the size of the temperature-adjustable pore opening to the size necessary for separation and contacting a gaseous mixture with the material to selectively adsorb one or more gases from the mixture with a molecular size smaller than the size of the temperature-dependent pore opening. For example, by setting a material to the desired temperature, mixtures of gases such as $H_2/N_2$, $H_2/CO$, $N_2/O_2$, $N_2/CH_4$, $CH_4/C_2H_4$, and $C_2H_4/C_3H$ can be separated from each other. Materials comprising temperature-adjustable pores may be used in other contexts described herein as well.

In some embodiments, the gas molecule comprises carbon. In some embodiments, the gas molecule comprises oxygen. A gas molecule may be selected from $CO_2$, $H_2$, $N_2$, $CO$, $O_2$, $CH_4$, $C_2H_4$, $SO_4$, $H_2S$, $CS_2$, $NH_3$, NO, and $C_3H_6$, or any combination thereof. Other gases may be employed as well.

A porous material is also provided wherein the material is capable of coordinating a solvent molecule in a pore. The material may be activated to coordinate the solvent molecule. Examples of such coordination are provided herein.

In some embodiments, a porous material comprises a single pore, wherein the single pore comprises a single gas molecule. Typically, a porous material comprising a single pore is referred to as a polyhedra material. In such materials, the Brunauer-Emmett-Teller (BET) surface area may range from about 150 $m^2/g$ to about 250 $m^2/g$. In some embodiments, the BET surface area ranges from about, at least about, or at most about 150, 175, 200, 225, or 250 $m^2/g$, or more, or any range derivable therein. A single gas molecule may be positioned between at least two metal ion dimers in the single pore of the material, wherein each dimer comprises an outer metal ion and an inner metal ion, wherein each inner metal ion participates in binding the single gas molecule, and wherein the outer metal ion and the inner metal ion are the same. What is intended by "outer" and "inner" metal ions is depicted in FIG. 1, wherein the inner metal ions are in closest proximity to the center of the material and the outer metal ions are located to the periphery.

The strength of metal ion binding may be determined by measuring heats of adsorption. The heat of adsorption will depend, in part, on the type of metal used and the gas molecule that is bound. Measurements of heats of adsorption are well-known in the art: typically, isotherms of gases are measured at different temperatures and data collected may be used to calculate the heat of adsorption. Such measurements are typically conducted at low pressure, such as a pressure that is lower than 1 atm. In some embodiments, the low pressure is less than 1, 0.9, 0.8, 0.7, 0.6, 0.5, 0.4, 0.3, 0.2, or 0.1 atm, or any range derivable therein. In some embodiments, the low pressure is less than 0.3 atm. In some embodiments, the heat of adsorption of a single gas molecule is at least about 7 kJ/mol. In some embodiments, the heat of adsorption is about, at most about, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 kJ/mol, or more. For example, the heat of adsorption for a $Cu_2$ dimer-containing material may be about 7 kJ/mol for binding an $H_2$ molecule. The heat of adsorption for a $Cu_2$ dimer-containing material may be about 35 kJ/mol for binding a $CO_2$ molecule. The heat of adsorption for a $Cu_2$ dimer-containing material may be about 30 kJ/mol for binding a $CH_4$ molecule. As another example, the heat of adsorption for a $Mo_2$ dimer-containing material may be less than 5 kJ/mol for binding an $H_2$ molecule.

A variety of metal ions may be employed. A metal ion may be selected from the group consisting of Mo, Cu, Zn, Co, Ru, and Rh, or a subset thereof. In some embodiments, a metal ion is selected from the group consisting of Cu, Zn, Co, Ru, and Rh. Any one or more of these metals may be specifically excluded from an embodiment. In some embodiments, the outer and inner metal ions may be further defined as excluding one or more of the following: Mo(II), Ag(I), Au(II), Li(I), Na(I), K(I), and Al(III). For example, in some embodiments, Mo is excluded as an optional outer and inner metal ion. In some embodiments, each metal ion of each dimer is Cu(II) or Ru(II). In particular, metals such as Cu, Zn, Co, Ru, and Rh provide open metal sites after removal of coordinated solvent molecules in the porous materials. These open sites may be used as "anchors" to interact with a small gas molecule (e.g. $H_2$, $CO_2$) to give strong adsorption (i.e. a strong trap). Based on their coordination geometric characteristics, these metal ions assist in providing the desired structure and trapping effects in the porous materials.

In some embodiments, a metal ion is selected from the group consisting of Cu(II) and Ru(II).

In some embodiments, each metal ion dimer is quadruply bonded by four bis(monodentate) ligands. Each bis(monodentate) ligand may be the same or different. In some embodiments, each bis(monodentate) ligand is the same. Bis(monodentate) ligands are advantageous for the construction of porous materials that trap single gas molecules as these ligands have a geometrically-fixed structure and metal ion linkage that provide desirable adsorptive properties.

In some embodiments, each metal ion is multiply bonded. For example, each metal ion may be sextuply bonded by four ligands. Each of the ligands may be the same or different. Each metal ion dimer may be bonded by a combination of poly(monodentate), poly(bidentate) ligands and/or bis(monodentate) ligands.

In some embodiments, at least one of the bis(monodentate) ligands is selected from a compound of formula (I) or (II):

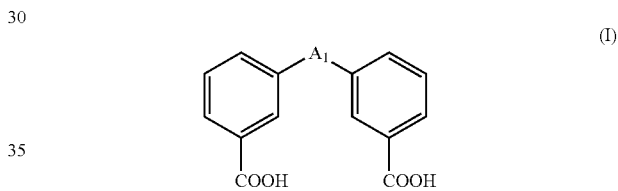

(I)

wherein $A_1$ is selected from naphthalenyl, quinolinyl, naphthyridinyl, anthracenyl, and acridinyl;

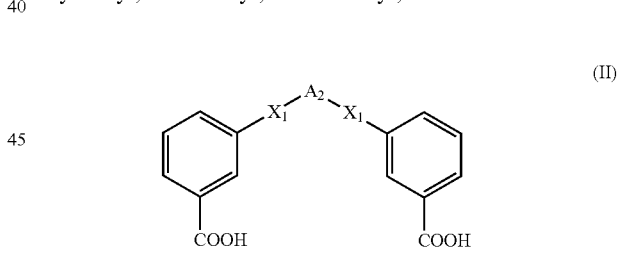

(II)

wherein $A_2$ is selected from phenyl, pyridinyl, naphthalenyl, naphthyridinyl, and acridinyl, and
$X_1$ is selected from ethynyl,

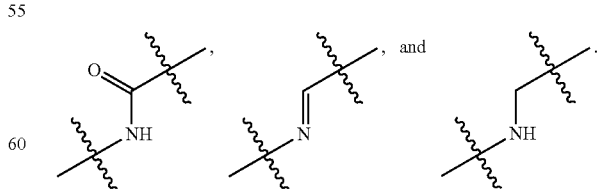

Any one or more combinations of $A_2$ and $X_1$ may be employed or specifically excluded. In some embodiments, at least one of the bis(monodentate) ligands is selected from a compound of formula (I).

In some embodiments, the compound of formula (I) is selected from the following, or any combination thereof:

[Structure A: 2,7-bis(3-carboxyphenyl)naphthalene]

[Structure B: 2,7-bis(3-carboxyphenyl)quinoline]

[Structure C: 3,3'-bis(3-carboxyphenyl)-1,8-naphthyridine]

[Structure D: 2,7-bis(3-carboxyphenyl)-1,8-naphthyridine]

[Structure E: 2,7-bis(3-carboxyphenyl)anthracene]

[Structure F: 3,6-bis(3-carboxyphenyl)acridine]

[Structure G: 2,6-bis((3-carboxyphenyl)ethynyl)pyridine]

[Structure H: 2,6-bis((3-carboxyphenylimino)methyl)pyridine]

[Structure I: 2,7-bis((3-carboxyphenyl)ethynyl)naphthalene]

[Structure J: 2,7-bis((3-carboxyphenyl)ethynyl)-1,8-naphthyridine]

[Structure K: N,N'-bis(3-carboxyphenyl)-1,3-bis(aminomethyl)benzene]

[Structure L: 3,6-bis((3-carboxyphenyl)ethynyl)acridine]

In some embodiments, at least one of the bis(monodentate) ligands is selected from a compound of formula (II).

The compound of formula (II) may be selected from the following, for example, or any combination thereof:

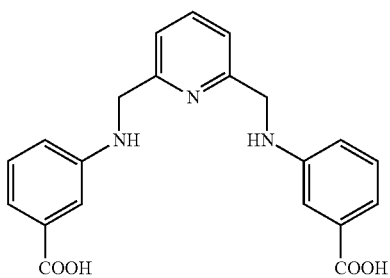

M

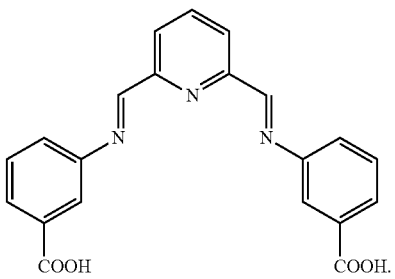

N

In some embodiments, at least one of the poly(monodentate) or poly(bidentate) ligands is a compound of formula (III):

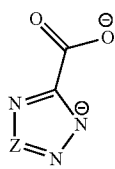

(III)

wherein Z is selected from —N and —CH.

In some embodiments, the compound of formula (III) is tetrazolate-5-carboxylate (tzc):

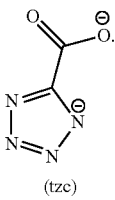

(tzc)

In some embodiments, at least one bis(monodentate) ligand is a compound of formula (IV):

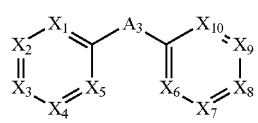

(IV)

wherein $X_1$-$X_{10}$ are independently selected from —C and —N, with the proviso that at least one of $X_1$-$X_5$ and at least one of $X_6$-$X_{10}$ is —N, $A_3$ is an alkyl or alkenyl group with 2 to 7 carbon atoms, which is optionally mono- or polysubstituted by —F, —Cl, —Br, —I, —NH$_2$, —OH, —CHO, an alkyl group with 1 to 5 carbon atoms, —O—CH$_3$, —CN, —NCO, —NO$_2$, —NO, —CH═CH$_2$ or —N$_3$, and wherein one or more non-adjacent —CH$_2$— groups is optionally replaced, in each case independently from another by —O—, —S—, —Se—, or —C═O.

In some embodiments, the compound of formula (IV) is selected from sub-formulae (IVi), (IVii) and (IViii):

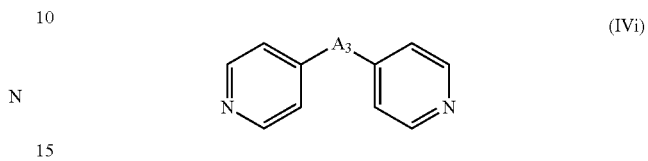

(IVi)

wherein $A_3$ is an alkyl group with 2 to 3 carbon atoms or an alkenyl group with 2 carbon atoms;

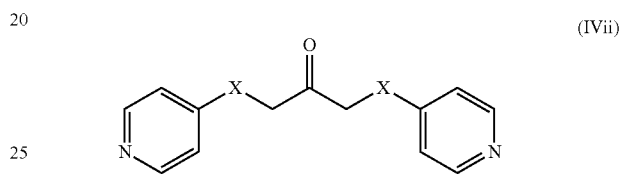

(IVii)

wherein X is selected from —C—, —O—, —S— and —Se—;

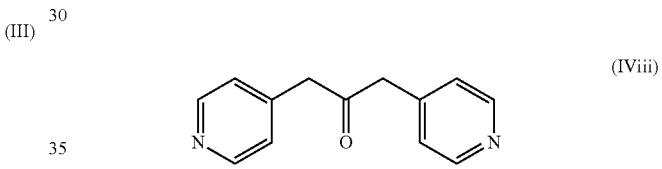

(IViii)

In some embodiments, the compound selected of formula (IVi) is 1,3-di(pyridyl)propane (dpp):

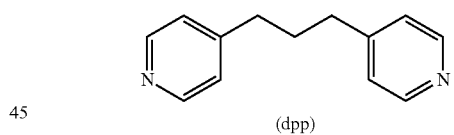

(dpp)

Advantageously, when a compound of formula (IV) includes a short alkyl chain such as propane, linking the two pyridine rings, the flexibility of the linking propane chain allows an elastic trapping effect to be achieved. Upon CO$_2$ adsorption, for example, the "elastic" nature of the pore leads to a unique, site-selective single molecule trapping of the gas molecules. The pore form continues to change to fit the single molecule (e.g. pore distances of 9.01(1)/8.444(1)×13.92(1)/13.54(3) Å), by fitting exactly one gas molecule per pore.

A porous material may, in some embodiments, comprise a plurality of pores, wherein at least one pore comprises a single gas molecule. Typically, a porous material comprising a plurality of pores is referred to as a framework material. In some embodiments, a majority of the plurality of pores each comprises a single gas molecule. In some embodiments, the BET surface area is about, at most about, or at least about 2500, 2600, 2700, 2800, 2900, 3000, 3100, 3200, 3300, 3400, or 3500, or more, or any range derivable therein. In some embodiments the BET surface area ranges from about 2500 m$^2$/g to about 3500 m$^2$/g. A BET surface area ranging from 2500 to 3500 m²/g, for example, provides high uptake for small molecules, such that the porous materials yield a high working capacity in adsorptive separations. In some embodiments, at least one pore comprises a single gas molecule positioned between two metal ion dimers in the material, wherein each dimer comprises an outer metal ion and an inner metal ion, wherein each inner metal ion participates in binding the single gas molecule, and wherein the outer metal ion and the inner metal ion are the same. The heat of adsorption of the single gas molecule may be as described herein. The metal ions may be as described herein. In some embodiments, each metal ion dimer is quadruply bonded by four tetra(monodentate) ligands, which may be the same or different. Tetra (monodentate) ligands are advantageous for the construction of porous materials that trap single gas molecules as these ligands have a geometrically-fixed structure and metal ion linkage that provide desirable adsorptive properties. In some embodiments, at least one of the tetra(monodentate) ligands is selected from a compound of formula (V) or (VI):

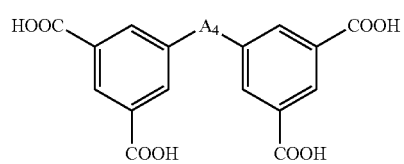
(V)

wherein $A_4$ is selected from pyridinyl, naphthalenyl, quinolinyl, naphthpyridinyl, anthracenyl, and acridinyl;

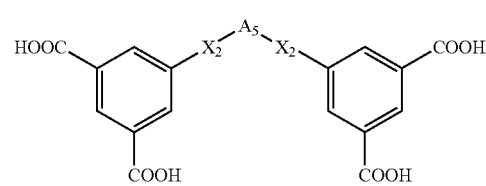
(VI)

wherein $A_5$ is selected from phenyl, pyridinyl, naphthalenyl, naphthpyridinyl, and acridinyl, and wherein $X_2$ is selected from ethynyl,

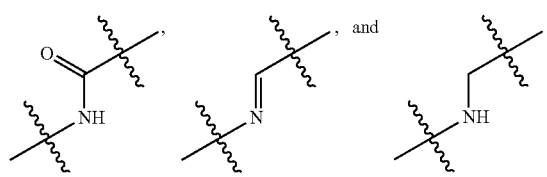

Any one or more combinations of $A_5$ and $X_2$ may be employed or specifically excluded. In some embodiments, at least one of the tetra(monodentate) ligands is selected from a compound of formula (V). The compound of formula (V) may be selected from the following, for example, or any combination thereof:

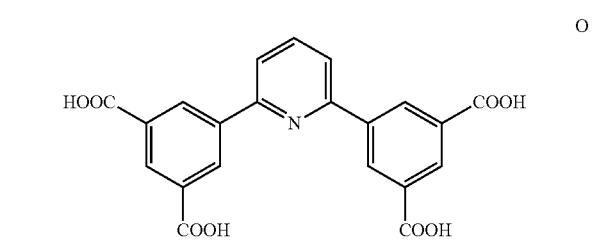
O

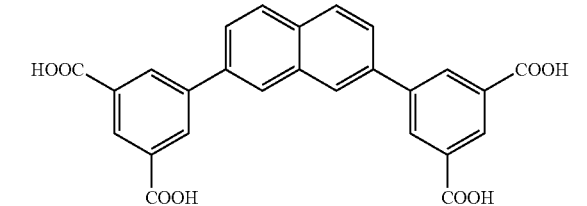
P

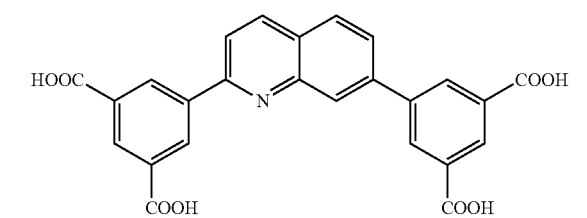
Q

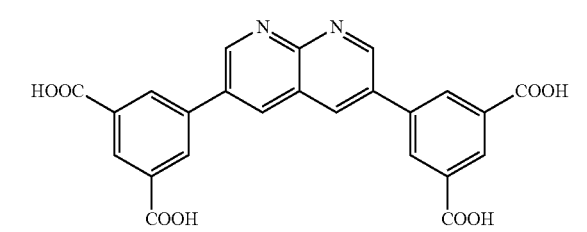
R

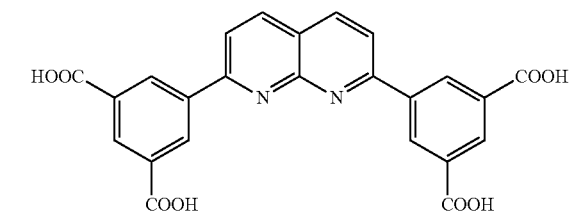
S

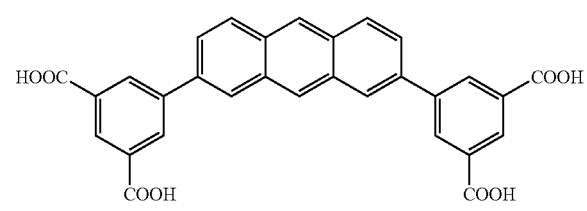
T

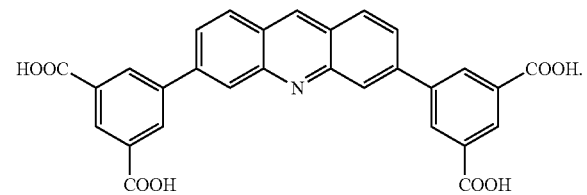
U

In some embodiments, at least one of the tetra(monodentate) ligands is selected from a compound of formula (VI).
The compound of formula (VI) may be selected from the following, for example, or any combination thereof:
V
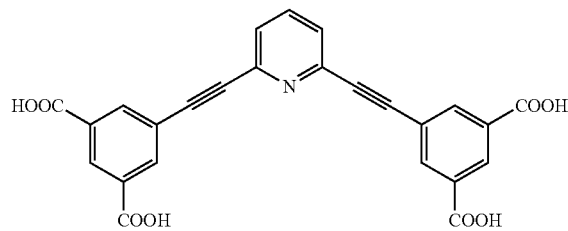
W
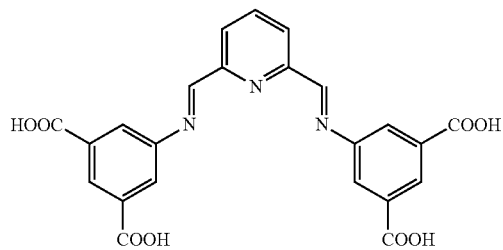
X
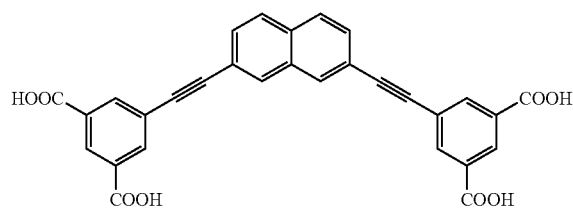
Y
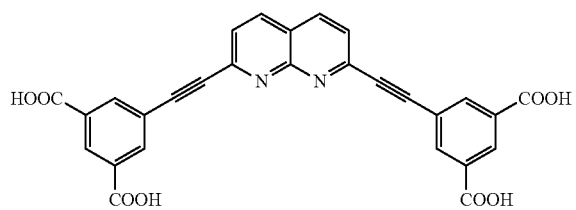
Z
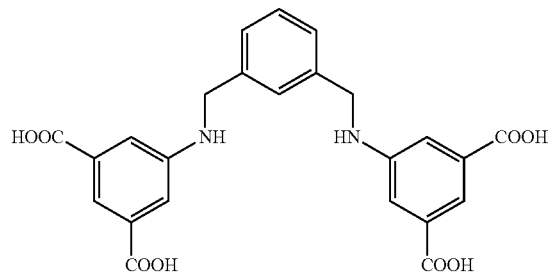
AA
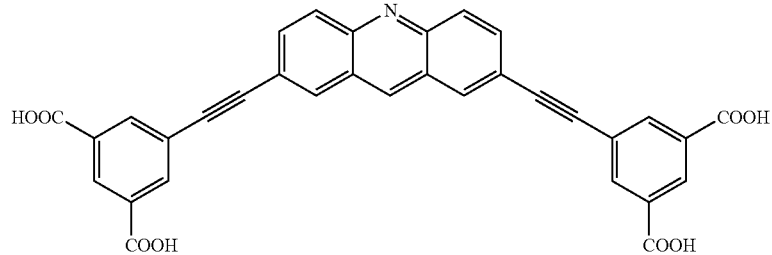
BB
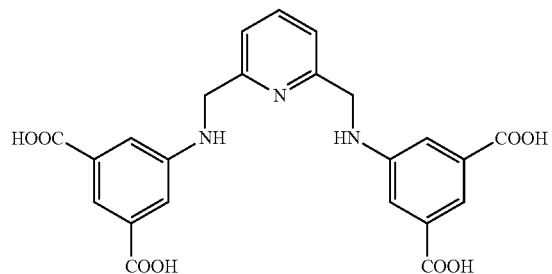
CC
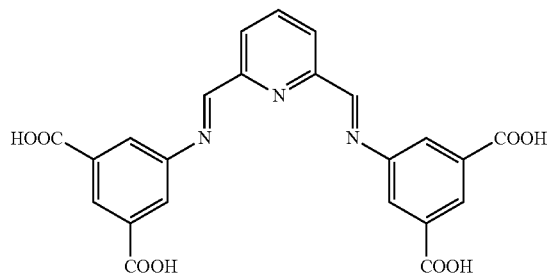

-continued

DD
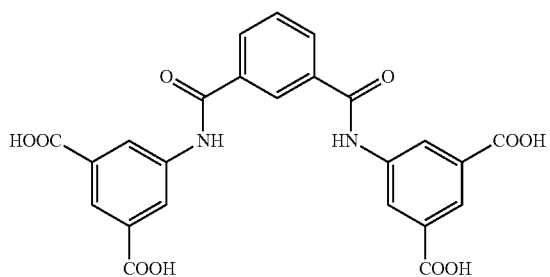

EE
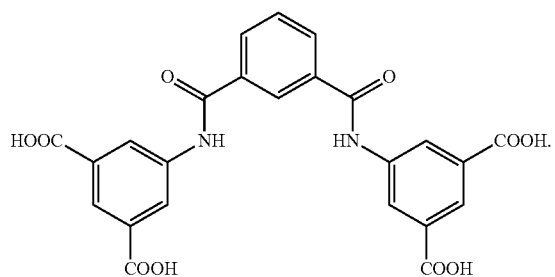

In some embodiments, each metal ion dimer is bonded by six ligands, which may be the same or different. In some embodiments, each metal ion dimer is bonded by a combination of poly(monodentate), poly(bidentate) ligands and/or bis(monodentate) ligands. In some embodiments, the poly-monodentate and/or the poly(bidentate) ligands are a compound of formula (III):

(III)
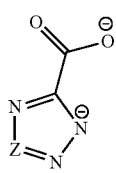

wherein Z is selected from —N and —CH.

In some embodiments, the compound of formula (III) is tetrazolate-5-carboxylate (tzc):

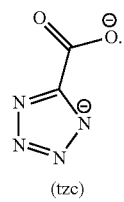
(tzc)

In some embodiments, the bis(monodentate) ligands are of formula (IV):

(IV)
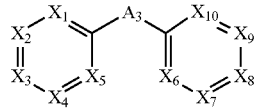

wherein $X_1$-$X_{10}$ are independently selected from —C and —N, with the proviso that at least one of $X_1$-$X_5$ and at least one of $X_6$-$X_{10}$ is —N,
$A_3$ is an alkyl or alkenyl group with 2 to 7 carbon atoms, which is optionally mono- or polysubstituted by —F, —Cl, —Br, —I, —NH$_2$, —OH, —CHO, an alkyl group with 1 to 5 carbon atoms, —O—CH$_3$, —CN, —NCO, —NO$_2$, —NO, —CH=CH$_2$ or —N$_3$, and wherein one or more non-adjacent —CH$_2$— groups is optionally replaced, in each case independently from another by —O—, —S—, —Se—, or —C=O.

In some embodiments, the compound of formula (IV) is selected from sub-formulae (IVi), (IVii) and (IViii):

(IVi)
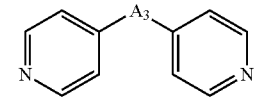

wherein $A_3$ is an alkyl group with 2 to 3 carbon atoms or an alkenyl group with 2 carbon atoms;

(IVii)
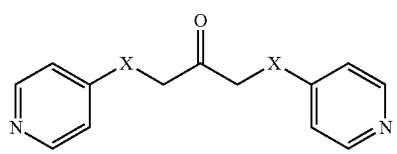

wherein X is selected from —C—, —O—, —S— and —Se—;

(IViii)
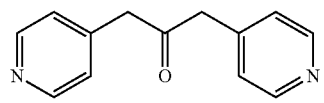

In some embodiments, the compound of formula (IVi) is 1,3-di(pyridyl)propane (dpp):

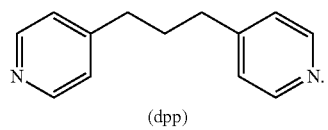 [SMILES: c1cc(CCCc2ccncc2)ccn1]
(dpp)

In an embodiment, each metal ion dimer is bonded by a combination of poly(monodentate), poly(bidentate) ligands and bis(monodentate) ligands. In an embodiment, each metal ion dimer is bonded by three ligands of formula (III) and a ligand of formula (IV). In this embodiment, two of the ligands of formula (III) are bidentate and one of the ligands of formula (III) is monodentate.

Also provided is a method of binding a single gas molecule in a porous material, comprising contacting the porous material with a plurality of gas molecules, wherein the porous material comprises (i) a single pore having a single pore size or (ii) a plurality of pores having an average pore size, wherein the single pore size or the average pore size is proportioned to accommodate a single gas molecule to the exclusion of additional gas molecules, such as gas molecules or liquid molecules. In some embodiments, the plurality of gas molecules is further defined as a mixture of gas molecules, and the porous material selectively binds the single gas molecule. Such methods may be used, for example, in the context of gas storage.

Typically, the application of pressure is employed to facilitate contact of a porous material with a plurality of gas molecules. In some embodiments, pressure ranges up to about 1,000 mm Hg. In some embodiments, pressure ranges from about, at most about, or at least about 100, 200, 300, 400, 500, 600, 700, 800, 900, or 1,000 mm HG, or more, or any range derivable therein.

Also provided are synthetic methods of preparing the porous materials as described herein. The synthetic methods illustrated in the Examples below, for example, are provided. In addition, such methods may be generally followed to produce other porous materials that are similar in structure to those disclosed herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In any embodiment discussed in the context of a numerical value used in conjunction with the term "about," it is specifically contemplated that the term about can be omitted.

Following long-standing patent law, the words "a" and "an," when used in conjunction with the word "comprising" in the claims or specification, denotes one or more, unless specifically noted.

DESCRIPTION OF THE DRAWINGS

The foregoing aspects and many of the attendant advantages will become more readily appreciated as the same becomes better understood by reference to the following detailed description, when taken in conjunction with the accompanying drawings.

FIG. 2 is based, in part, on G. H. Clever, S. Tashiro, M. Shionoya, *Angew. Chem. Int. Ed.* 2009, 48, 7010-7012;

EXAMPLES

I. Introduction

Figure 1:
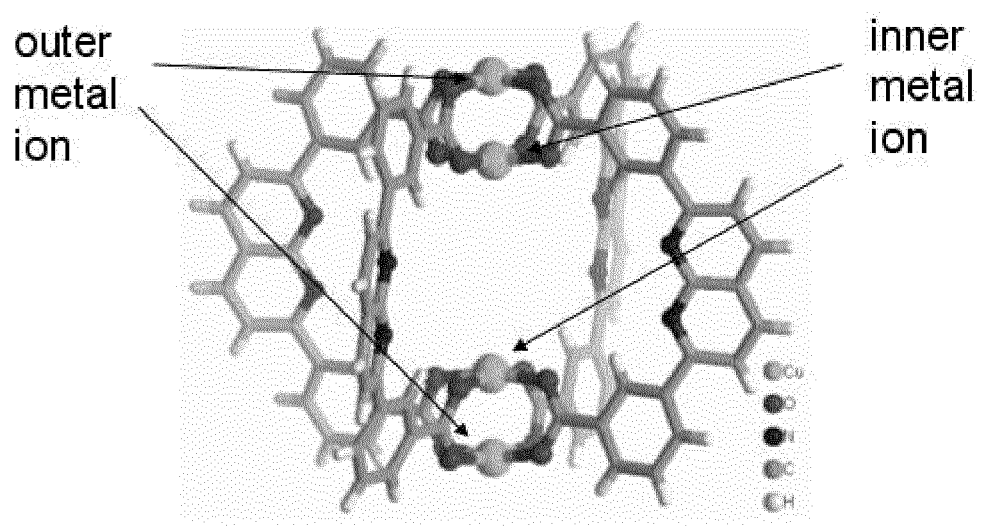
FIG. 1: Schematic illustrating "outer" and "inner" metal ions.
Figure 2:
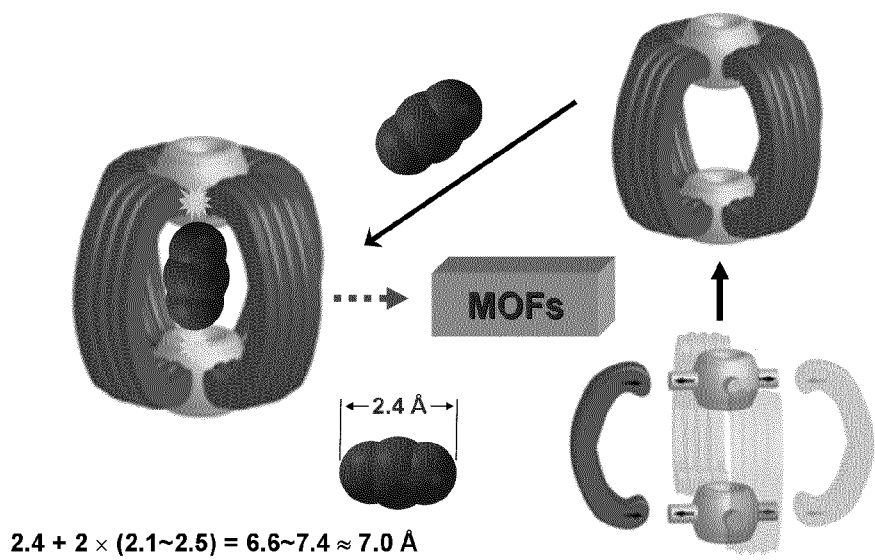
FIG. 2: Schematic presentation of a single-molecule trap for small molecule ($CO_2$) capture.

Presented first is an exemplary configuration for a single-molecule trap for $CO_2$ capture (FIG. 1 and SMT-1 to 4), followed by a description of the synthesis of MOF materials comprising a single-molecule trap (MOF-5, MOF-6) and then by a description of the synthesis of "elastic" MOF material MOF-7.

2. Synthesis of Exemplary Organic Ligands

As examples, the following five ligands were synthesized.

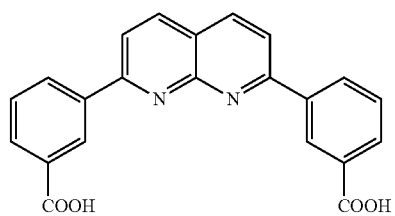

3,3'-(1,8-naphthyridine-2,7-diyl)dibenzoic acid ($H_2L^1$)

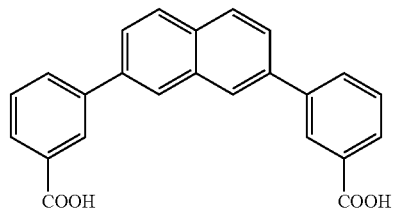

3,3'-(naphthalene-2,7-diyl)dibenzoic acid ($H_2L^2$)

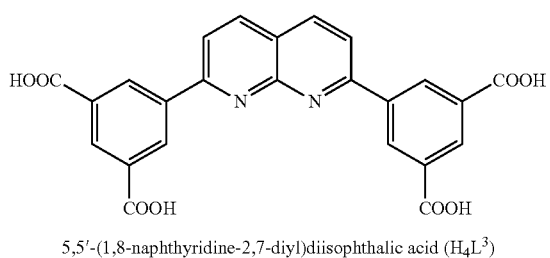

5,5'-(1,8-naphthyridine-2,7-diyl)diisophthalic acid (H$_4$L$^3$)

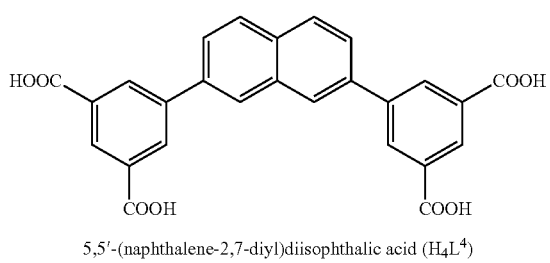

5,5'-(naphthalene-2,7-diyl)diisophthalic acid (H$_4$L$^4$)

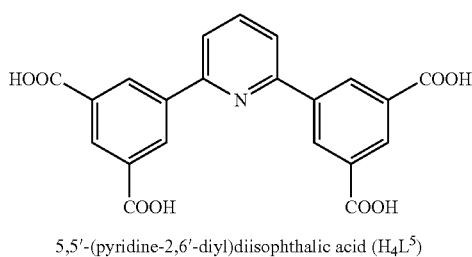

5,5'-(pyridine-2,6'-diyl)diisophthalic acid (H$_4$L$^5$)

2.1. 3,3'-(1,8-Naphthyridine-2,7-diyl)dibenzoic acid (H$_2$L$^1$)

(a) Dimethyl 3,3'-(1,8-naphthyridine-2,7-diyl)dibenzoate

To a 250 mL Schlenk flask, 2,7-dibromo-1,8-naphthyridine (2.00 g, 6.94 mmol), 3-(methoxycarbonyl)phenylboronic acid (3.13 g, 17.40 mmol), CsF (4.00 g), and Pd(PPh$_3$)$_4$ (200 mg) were added. The flask was connected to a Schlenk line and evacuated of air then refilled with nitrogen gas. 130 mL of 1,2-dimethoxyethane (DME) was degassed (two hours) and added to the flask through a canula. The flask was equipped with a water condenser and refluxed under nitrogen gas atmosphere for 3 days. The solvent was removed on rotary evaporator. 100 mL of H$_2$O was added and then extracted with CHCl$_3$. The organic phase was dried with MgSO$_4$. After removal of the CHCl$_3$ solvent, the crude product was purified by column chromatography (silica, ethyl acetate/hexane, 20%) to give a white solid product with a yield of 83% (2.30 g) based on 2,7-dibromo-1,8-naphthyridine. $^1$H NMR (300 MHz, CD$_3$Cl): δ 3.97 (s, 6H), 7.62 (t, 2H), 8.03 (d, 2H), 8.17 (d, 2H), 8.30 (d, 2H), 8.57 (d, 2H), 8.88 (s, 2H).

(b) 3,3'-(1,8-Naphthyridine-2,7-diyl)dibenzoic acid (H$_2$L$^1$)

2.0 g dimethyl 3,3'-(1,8-naphthyridine-2,7-diyl)dibenzoate was dissolved in 60 mL of mixed solvent of THF and MeOH (v/v=1:1), 20 mL of 2N NaOH aqueous solution was added. The mixture was stirred at room temperature overnight. After the organic phase was removed, the aqueous phase was acidified with dilute hydrochloric acid to give white precipitate, which was filtered and washed with water several times. Yield: 1.73 g, 93%. $^1$H NMR (300 MHz, DMSO-d$^6$): δ 7.74 (t, 2H), 8.12 (d, 2H), 8.36 (d, 2H), 8.60 (d, 2H), 8.64 (d, 2H), 8.97 (s, 2H).

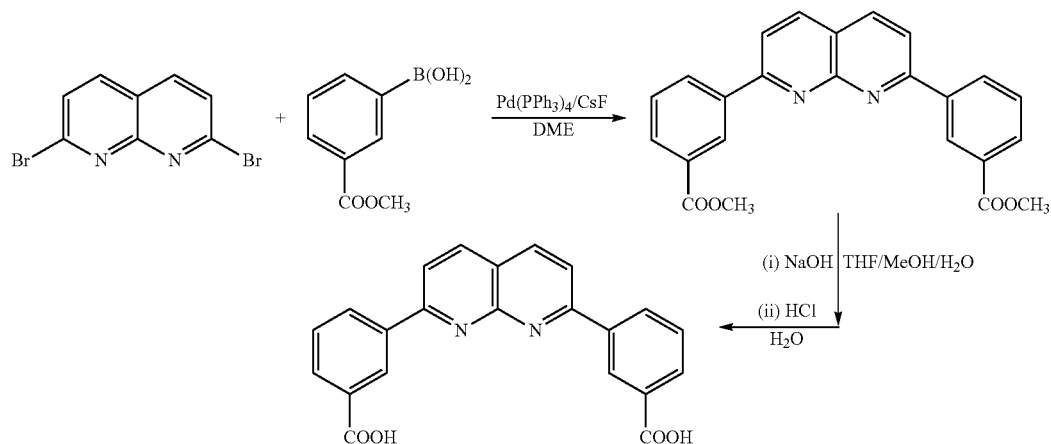 [SMILES: Brc1ccc2ccc(Br)nc2n1 ; COC(=O)c1cccc(B(O)O)c1 ; "DME" ; COC(=O)c1cccc(-c2ccc3ccc(-c4cccc(C(=O)OC)c4)nc3n2)c1 ; O=C(O)c1cccc(-c2ccc3ccc(-c4cccc(C(=O)O)c4)nc3n2)c1 ; O]

2.2. 3,3'-(Naphthalene-2,7-diyl)dibenzoic acid ($H_2L^2$)

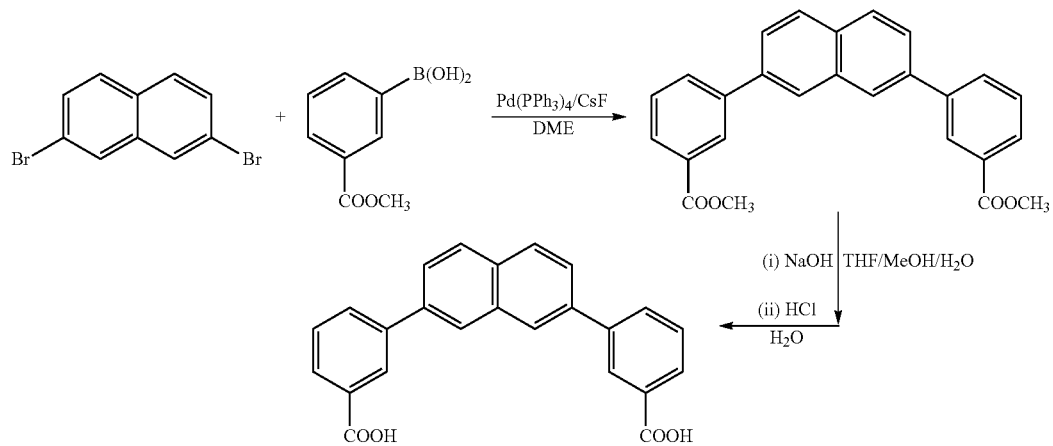 [SMILES: Brc1ccc2ccc(Br)cc2c1 ; COC(=O)c1cccc(B(O)O)c1 ; "DME" ; COC(=O)c1cccc(-c2ccc3ccc(-c4cccc(C(=O)OC)c4)cc3c2)c1 ; O=C(O)c1cccc(-c2ccc3ccc(-c4cccc(C(=O)O)c4)cc3c2)c1 ; O]

(a) Dimethyl 3,3'-(naphthalene-2,7-diyl)dibenzoate

To a 250 mL Schlenk flask, 2,7-dibromonaphthalene (2.00 g, 6.99 mmol), 3-(methoxycarbonyl)phenylboronic acid (3.15 g, 17.48 mmol), CsF (4.00 g) and Pd(PPh$_3$)$_4$ (200 mg) were added. The flask was connected to a Schlenk line and evacuated of air then refilled with nitrogen. 150 mL of 1,2-dimethoxyethane (DME) was degassed (two hours) and added to the flask through a canula. The flask was equipped with a water condenser and refluxed under nitrogen for 2 days. The solvent was removed on a rotary evaporator. 100 mL of H$_2$O was added and then extracted with CHCl$_3$. The organic phase was dried with MgSO$_4$. After removal of the CHCl$_3$ solvent, the crude product was re-crystallized from the mixture solvent of ethyl acetate and hexane (v/v=1:9) to give a pure product with a yield of 72% (2.0 g) based on 2,7-dibromonaphthalene. $^1$H NMR (300 MHz, DMSO-d$^6$): δ 3.92 (s, 6H), 7.70 (t, 2H), 7.93 (d, 2H), 8.01 (d, 2H), 8.13 (m, 4H), 8.39 (m, 2H), 8.45 (d, 2H).

(b) 3,3'-(Naphthalene-2,7-diyl)dibenzoic acid ($H_2L^2$)

2.0 g of dimethyl 3,3'-(naphthalene-2,7-diyl)dibenzoate was dissolved in 60 mL of mixed solvent of THF and MeOH (v/v=1:1), 20 mL of 2N NaOH aqueous solution was added. The mixture was stirred at room temperature overnight. After the organic phase was removed, the aqueous phase was acidified with dilute hydrochloric acid to give white precipitate, which was filtered and washed with water several times. Yield: 1.71 g, 92%. $^1$H NMR (300 MHz, DMSO-d$^6$): δ 7.65 (t, 2H), 7.92 (d, 2H), 7.98 (d, 2H), 8.09 (m, 4H), 8.38 (m, 2H), 8.43 (d, 2H).

2.3. 5,5'-(1,8-naphthyridine-2,7-diyl)diisophthalic acid ($H_4L^3$)

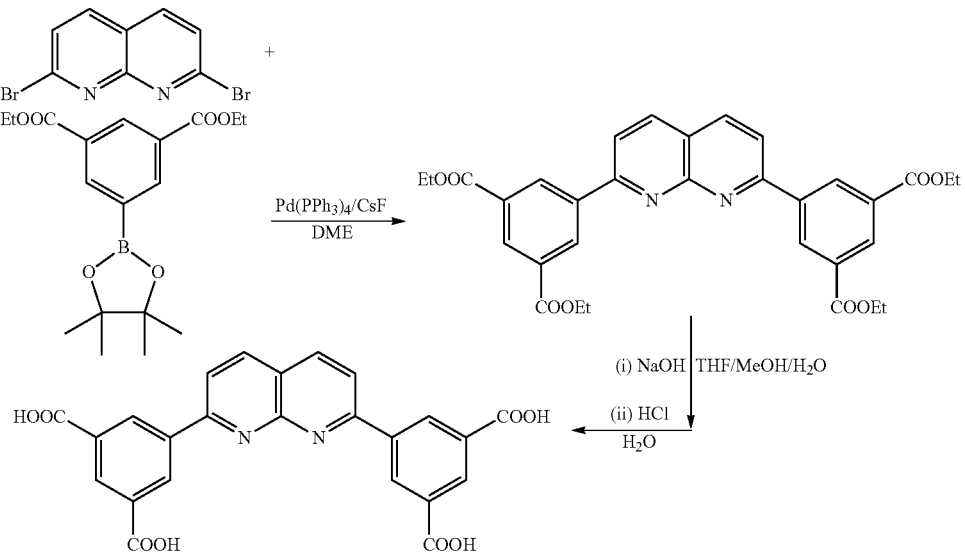

(a) Tetraethyl 5,5'-(1,8-naphthyridine-2,7-diyl)diisophthalate

To a 250 mL Schlenk flask, 2,7-dibromo-1,8-naphthyridine (2.00 g, 6.94 mmol), diethyl 5-(4,4,5,5-tetramethyl-1,3,2-dioxaborolan-2-yl)isophthalate (6.06 g, 17.40 mmol, this compound was synthesized according to literature method: J. Natera, L. Otero, L. Sereno, F. Fungo, N.-S. Wang, Y.-M. Tsai, T.-Y. Hwu, K.-T. Wong, *Macromolecules* 2007, 40, 4456-4463), CsF (4.00 g) and Pd(PPh$_3$)$_4$ (200 mg) were added. The flask was connected to a Schlenk line and evacuated of air then refilled with nitrogen. 140 mL of 1,2-dimethoxyethane (DME) was degassed (two hours) and added to the flask through a canula. The flask was equipped with a water condenser and refluxed under nitrogen for 3 days. The solvent was removed on a rotary evaporator. 100 mL of H$_2$O was added and then extracted with CHCl$_3$. The organic phase was dried with MgSO$_4$. After removal of the CHCl$_3$ solvent, the crude product was purified by column chromatography (silica, ethyl acetate/hexane, 20% and then 50%) to give a yellow solid product with a yield of 70% (2.77 g) based on 2,7-dibromo-1,8-naphthyridine. $^1$H NMR (300 MHz, DMSO-d$^6$): δ 1.42 (t, 12H), 4.46 (q, 8H), 8.43 (d, 2H), 8.60 (s, 2H), 8.69 (d, 2H), 9.07 (s, 4H).

(b) 5,5'-(1,8-Naphthyridine-2,7-diyl)diisophthalic acid (H$_4$L$^3$)

2.0 g of tetraethyl 5,5'-(1,8-naphthyridine-2,7-diyl)diisophthalate was dissolved in 60 mL of mixed solvent of THF and MeOH (v/v=1:1), 20 mL of 2N NaOH aqueous solution was added. The mixture was stirred at room temperature overnight. After the organic phase was removed, the aqueous phase was acidified with dilute hydrochloric acid to give white precipitate, which was filtered and washed with water several times. Yield: 1.5 g, 94%. $^1$H NMR (300 MHz, DMSO-d$^6$): δ 8.44 (d, 2H), 8.62 (s, 2H), 8.68 (d, 2H), 9.10 (s, 4H).

2.4. 5,5'-(naphthalene-2,7-diyl)diisophthalic acid (H$_4$L$^4$)

(a) Tetraethyl 5,5'-(naphthalene-2,7-diyl)diisophthalate

To a 250 mL Schlenk flask, 2,7-dibromonaphthalene (2.00 g, 6.99 mmol), diethyl 5-(4,4,5,5-tetramethyl-1,3,2-dioxaborolan-2-yl)isophthalate (6.09 g, 17.48 mmol), CsF (4.00 g) and Pd(PPh$_3$)$_4$ (200 mg) were added. The flask was connected to a Schlenk line and evacuated of air then refilled with nitrogen. 160 mL of 1,2-dimethoxyethane (DME) was degassed (two hours) and added to the flask through a canula. The flask was equipped with a water condenser and refluxed under nitrogen for 2 days. The solvent was removed on a rotary evaporator. 120 mL of H$_2$O was added and then extracted with CHCl$_3$. The organic phase was dried with MgSO$_4$. After removal of the CHCl$_3$ solvent, the crude product was washed with acetone and then hexane (3×20 mL for each) to give a pure product with a yield of 76% (3.02 g) based on 2,7-dibromonaphthalene. $^1$H NMR (300 MHz, DMSO-d$^6$): δ 1.39 (t, 12H), 4.42 (q, 8H), 7.90 (d, 2H), 8.11 (d, 2H), 8.45 (s, 4H), 8.52 (s, 4H).

(b) 5,5'-(Naphthalene-2,7-diyl)diisophthalic acid (H$_4$L$^4$)

2.0 g of tetraethyl 5,5'-(naphthalene-2,7-diyl)diisophthalate was dissolved in 60 mL of mixed solvent of THF and MeOH (v/v=1:1), 20 mL of 2N NaOH aqueous solution was added. The mixture was stirred at room temperature overnight. After the organic phase was removed, the aqueous phase was acidified with dilute hydrochloric acid to a white precipitate, which was filtered and washed with water several times. Yield: 1.46 g, 91%. $^1$H NMR (300 MHz, DMSO-d$^6$): δ 7.95 (d, 2H), 8.11 (d, 2H), 8.53 (m, 8H).

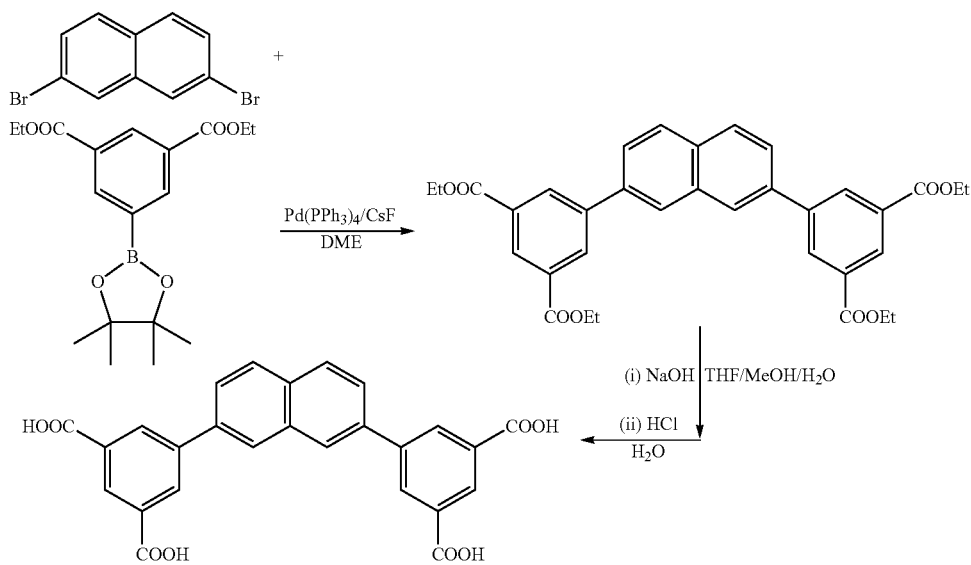

2.5. 5,5'-(pyridine-2,6'-diyl)diisophthalic acid ($H_4L^5$)

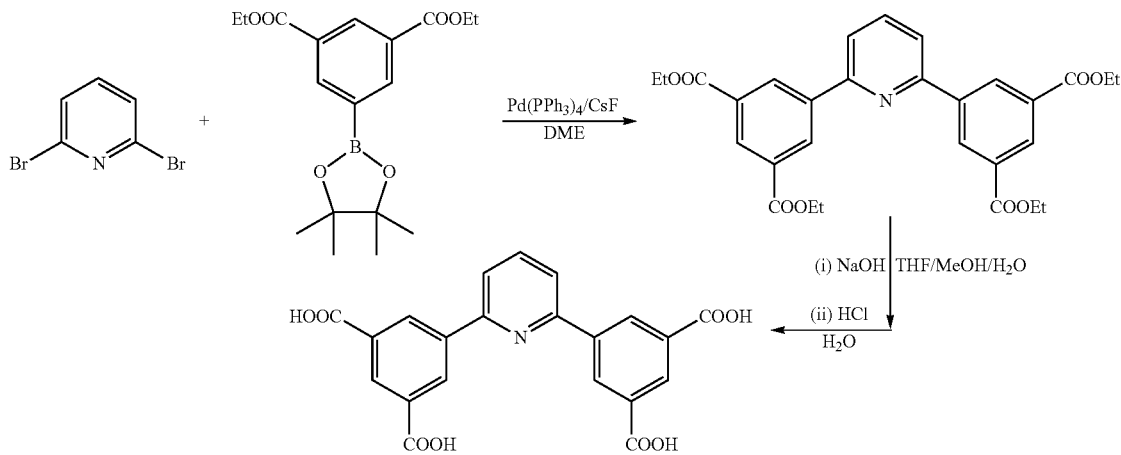 [SMILES: Brc1cccc(Br)n1 ; CCOC(=O)c1cc(B2OC(C)(C)C(C)(C)O2)cc(C(=O)OCC)c1 ; O=C(O)c1cc(C(=O)O)cc(-c2cccc(-c3cc(C(=O)O)cc(C(=O)O)c3)n2)c1 ; "DME" ; CCOC(=O)c1cc(C(=O)OCC)cc(-c2cccc(-c3cc(C(=O)OCC)cc(C(=O)OCC)c3)n2)c1 ; O]

(a) Tetraethyl 5,5'-(pyridine-2,6'-diyl)diisophthalate

To a 250 mL Schlenk flask, 2,6-dibromopyridine (2.00 g, 8.44 mmol), diethyl 5-(4,4,5,5-tetramethyl-1,3,2-dioxaborolan-2-yl)isophthalate (7.35 g, 21.10 mmol), CsF (4.00 g) and Pd(PPh$_3$)$_4$ (300 mg) were added. The flask was connected to a Schlenk line and evacuated of air then refilled with nitrogen. 160 mL of 1,2-dimethoxyethane (DME) was degassed (two hours) and added to the flask through a canula. The flask was equipped with a water condenser and refluxed under nitrogen for 3 days. The solvent was removed on rotary evaporator. 110 mL of H$_2$O was added and then extracted with CHCl$_3$. The organic phase was dried with MgSO$_4$. After removed the CHCl$_3$ solvent, the crude product was purified by column chromatography (silica, ethyl acetate/hexane, 20%) to give a white solid product with a yield of 72% (3.16 g) based on 2,6-dibromopyridine. $^1$H NMR (300 MHz, CD$_3$Cl): δ 1.43 (t, 12H), 4.44 (q, 8H), 8.10 (m, 3H), 8.58 (s, 2H), 8.92 (s, 4H).

(b) 5,5'-(Pyridine-2,6'-diyl)diisophthalic acid ($H_4L^5$)

2.0 g of tetraethyl 5,5'-(pyridine-2,6'-diyl)diisophthalate was dissolved in 60 mL of mixed solvent of THF and MeOH (v/v=1:1), 20 mL of 2N NaOH aqueous solution was added. The mixture was stirred at room temperature overnight. After the organic phase was removed, the aqueous phase was acidified with dilute hydrochloric acid to give a white precipitate, which was filtered and washed with water several times. Yield: 1.44 g, 92%. $^1$H NMR (300 MHz, DMSO-d$^6$): δ 8.12 (m, 3H), 8.57 (s, 2H), 8.91 (s, 4H).

3. Synthesis and Crystal Structures of Single-Molecular Trap (SMT) Molecules Four single-molecule trap compounds (SMT-1 to 4) were synthesized and structurally determined by single-crystal X-ray diffraction.

3.1. [Cu$_2$(L$^1$)$_2$(DMA)$_2$]$_2$ (SMT-1)

Figure 3:
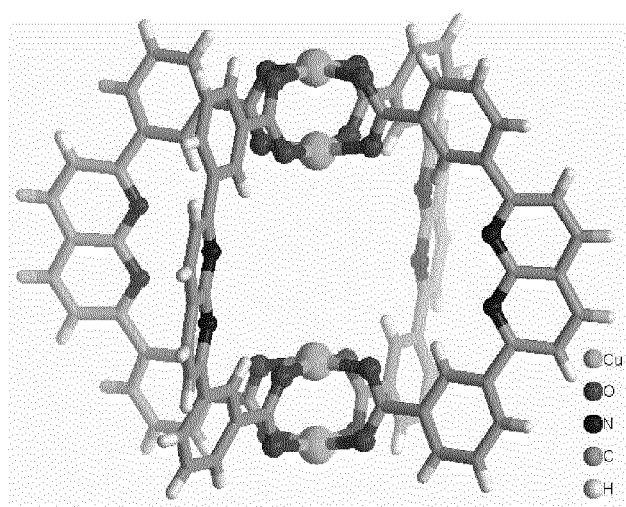
FIG. 3: Molecular structure of SMT-1 (solvent molecules omitted for clarity; the Cu—Cu distance in this trap is 6.8 Å)

A dimethylacetamide (DMA) (1.5 mL) solution of H$_2$L$^1$ (38 mg, 0.1 mmol) was mixed with a DMA solution (2.5 mL) of Cu$_2$(OAc)$_4$.2H$_2$O (20 mg, 0.05 mmol) in a glass vial (5 mL) and then the vial was allowed to stand at room temperature. After 10 days homogeneous green-blue crystals of SMT-1 were collected and washed with DMA and a little acetone (yield, ~40 mg). The structure of SMT-1 was determined by single-crystal X-ray diffraction (FIG. 3). As can be seen from FIG. 3, the molecule has a lantern-type structural arrangement with four bridging ligands surrounding two paddlewheel dicopper units to form a large 'paddlewheel' tetragonal cage or trap. Each copper atom is coordinated by four carboxylate oxygen atoms of different ligands in the equatorial position and one DMA molecule in the axial position when solvated, which can be removed to leave active open metal site (as in FIG. 3). The molecular dimensions of the molecule, excluding coordinated solvents in height (Cu . . . Cu) and diameter (C . . . C between two opposite ligands) was 11.9×19.8 Å, and the inner cavity was 6.7×12.5 Å (atom-to-atom distances across opposite Cu and H (or N) atoms of ligands). In particular, the distances between two opposite copper sites in each cavity was 7.4, being suitable for the accommodation of one CO$_2$ molecule through the adsorption of two O atoms to the copper sites.

Crystal Data:
crystalline system: triclinic; space group: P-1; a=14.002(7), b=15.539(8), c=15.764(8) Å; α=96.616(7), β=110.783(7), γ=105.072(7)°; V=3014(3) Å$^3$.

3.2. Ru(L$^1$)(DMA)$_2$(BF$_4$)$_{0.5}$ (SMT-2)

Figure 4:
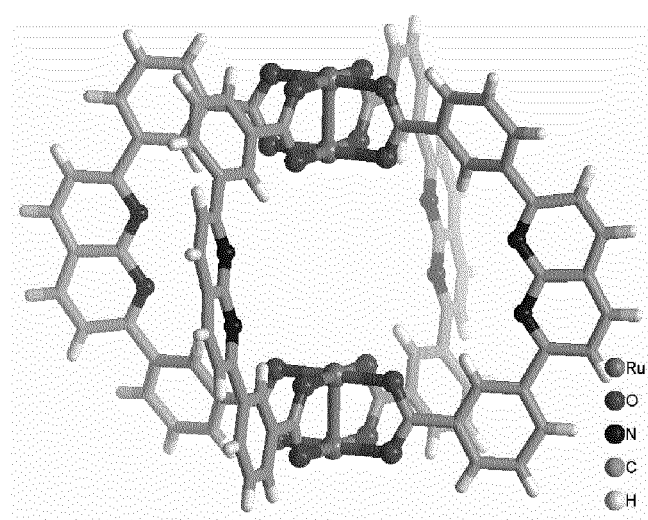
FIG. 4: Molecular structure of SMT-2 (solvent molecules omitted for clarity; the Ru—Ru distance in this trap is 7.2 Å)

A mixture of 1:2 molar ratio of Ru$_2$Cl(OAc)$_4$ (12 mg, 0.025 mmol) and H$_2$L$^1$ (19 mg, 0.050 mmol) was added to a glass tube, to which 2 drops of HBF$_4$ (40% in water) and 1.8 mL of DMA were added successively. The mixture was degassed by two freeze-pump-thaw cycles. The tube was then frozen again in liquid nitrogen and sealed under vacuum. Once the temperature reached room temperature the sealed mixture was sonicated to allow all solids to dissolve. The tube was heated in a furnace at 85° C. for 5 days and cooled to room temperature spontaneously. In an N$_2$-filled glove box, single crystals were collected by filtration, washed with 2×2 mL of DMA, and then quickly dried on a piece of filter paper to afford 10 mg of crystalline product of SMT-2. The structure of SMT-2 was determined by single-crystal X-ray diffraction (FIG. 4).

Crystal Data:
crystalline system: triclinic; space group: P-1; a=13.49(2), b=14.65(3), c=27.09(5) Å; α=90.40(2), β=90.18(2), γ=95.78(2)°; V=5328(16) Å$^3$.

3.3. Mo(L$^1$)(DMA)$_2$ (SMT-3)

Figure 5:
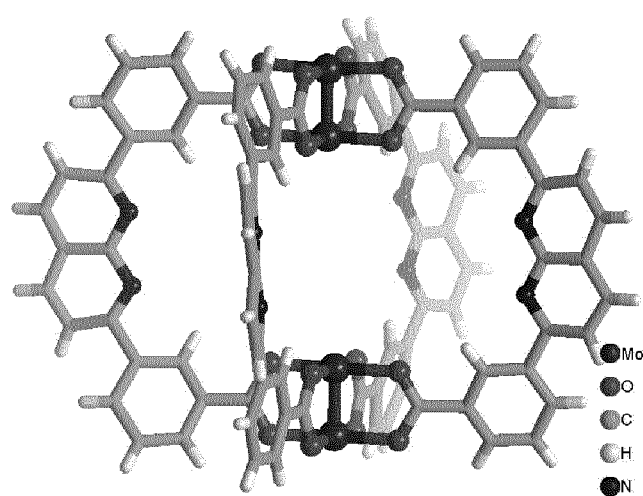
FIG. 5: Molecular structure of SMT-3 (solvent molecules omitted for clarity; the Mo—Mo distance in this trap is 7.4 Å)

A mixture of 1:2 molar ratio of Mo$_2$(O$_2$CCF$_3$)$_4$ (16 mg, 0.025 mmol) and H$_2$L$^1$ (19 mg, 0.050 mmol) was added to a glass tube, to which 1 drop of $HBF_4$ (40% in water) and 1.8 mL of DMA were added successively. The mixture was degassed by two freeze-pump-thaw cycles. The tube was then frozen again in liquid nitrogen and sealed under vacuum. Once the temperature reached room temperature the sealed mixture was sonicated to allow all solids to dissolve. The tube was heated in a furnace at 85° C. for 12 hours and cooled to room temperature spontaneously. In an $N_2$-filled glove box, single crystals were collected by filtration, washed with 2×3 mL of DMA, and then quickly dried on a piece of filter paper to afford 14 mg of crystalline product of SMT-3. The structure of 3 was determined by single-crystal X-ray diffraction (FIG. 5).

Crystal Data:
crystalline system: triclinic; space group: P-1; a=12.71(3), b=15.26(4), c=25.08(6) Å; α=85.22(4), β=83.99(4), γ=88.81(4)°; V=4820(21) Å$^3$.

3.4. $[Cu_2(L^2)_2(DMA)_2]_2$ (SMT-4)

Figure 6:
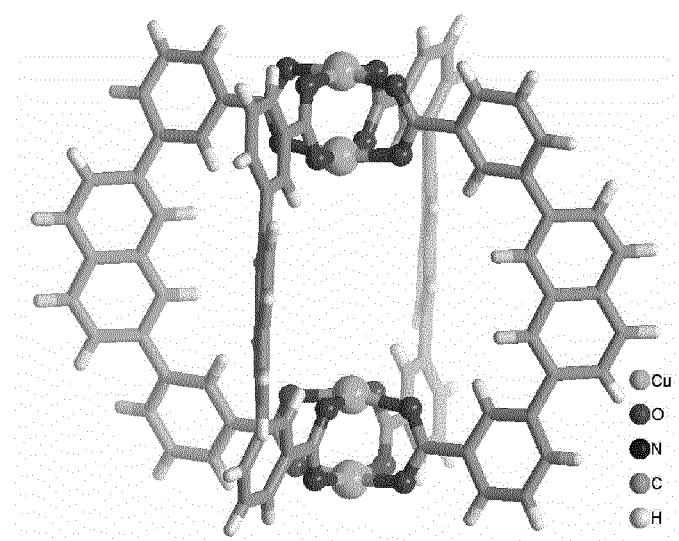
FIG. 6: Molecular structure of SMT-4 (solvent molecules omitted for clarity; the Cu—Cu distance in this trap is 7.4 Å)

A dimethylacetamide (DMA) (1.5 mL) solution of $H_2L^2$ (37 mg, 0.1 mmol) was mixed with a DMA solution (3 mL) of $Cu_2(OAc)_4·2H_2O$ (22 mg, 0.05 mmol) in a glass vial (5 mL) and then the vial was allowed stand at room temperature. After 10 days homogeneous small green-blue block crystals of SMT-4 were collected and washed with DMA and a little acetone (yield, ~42 mg). Bigger crystals for single-crystal X-ray diffraction were obtained by a layer-diffusion method. The structure of SMT-4 was determined by single-crystal X-ray diffraction (FIG. 6). As for compound SMT-1, the molecule has a lantern-type structural arrangement with four bridging ligands surrounding two paddlewheel dicopper units to form a large 'paddlewheel' tetragonal trap. The molecular dimensions of the molecule excluding coordinated solvents in height (Cu . . . Cu) and diameter (C.*C between two opposite ligands) was 12.6×19.4 Å, and the inner cavity was 7.4×11.7 Å (atom-to-atom distances across opposite Cu and H (or N) atoms of ligands). The distances between two opposite copper sites in each cavity was 7.4 Å.

Crystal Data:
crystalline system: monoclinic; space group: C2/c; a=22.203(2), b=20.122(2), c=30.441(2) Å; α=90, β=116.012(5), γ=90°; V=12223(2) Å$^3$.

4. Synthesis and Crystal Structures of Porous Materials (Metal-Organic Frameworks) with Built-in Single-Molecular Traps 4.1. $[Cu(L^4)_{1/2}(S)]_n$ (MOF-5, S is Coordinated Solvent Molecule)

Figure 7:
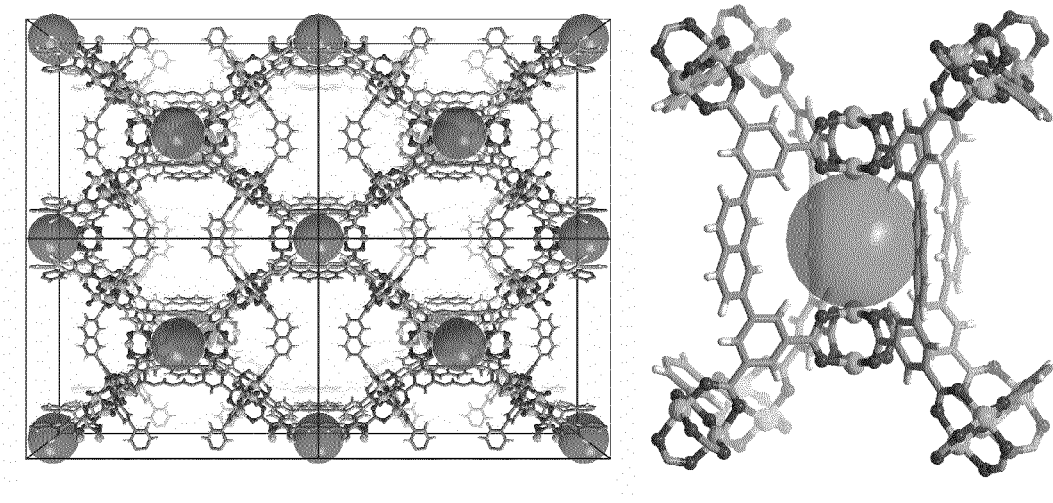
FIG. 7: Structure of MOF-5 (solvent molecules omitted for clarity)

In order to evaluate the use of SMTs in extended porous materials, ligand $H_2L^2$ was functionalized by the incorporation of two additional carboxylic acid groups to generate ligand $H_4L^4$. A mixture of $H_4L^4$ (72 mg, 0.16 mmol), $Cu(NO_3)_2·2.5H_2O$ (120 mg, 0.5 mmol), 1 mL of tetrafluoroboric acid ($HBF_4$, 48% w/w aqueous solution), and 2 mL of water in 17 mL of dimethylformamide (DMF) was sealed in a 20 mL glass vial and placed in an oven at 85° C. for 48 hours. The resulting green crystals of MOF-5 were collected and washed with DMA and a little bit of acetone, and then dried (yield 110 mg). FIG. 7 depicts single-crystal X-ray diffraction results.

Crystal Data:
crystalline system: orthorhombic; space group: Imm2; a=27.547(4), b=36.559(5), c=18.413(2) Å; α=90, β=90, γ=90°; V=18544(4) Å$^3$.

As shown in FIG. 7, four $L^4$ ligands firstly bridge two paddlewheel dinuclear copper units to form a molecular building unit similar to SMT-1, with eight additional carboxylate groups pointing to eight vertices of a cuboid lattice. Through these carboxylate groups, each unit is linked to eight similar ones by sharing eight dicopper units to form a 3D network. An additional two extending points in each of the eight dicopper units are further coordinated by carboxylate groups of the other $L^4$ ligands with a different configuration from that of constructing SMT units. Finally, $L^4$ ligands with the two types of configurations link paddlewheel dicopper units to generate two additional new polyhedral molecular cages or traps. Both cage-type polyhedra have 12 faces (dodecahedron) but a different numbers of edges and vertices. The first dodecahedron with 20 edges and 10 vertices can be described as a combination of two square pyramids and one rectangular prism by sharing two square faces. The cavity size of this polyhedral cage determined by atom-to-atom distances in height and width is about 20×24 Å. The second one is comprised of two truncated triangular prisms and one rectangular prism combined through sharing their quadrate faces. It has 22 edges, 12 vertices, and an evaluated cavity size of about 5×24 Å. The whole framework of the porous material is thus composed of three types of unit building blocks including the SMT unit, in which the distance between two opposite copper sites in the cavity is 7.4 Å, as in SMT-1. The analysis of porous structure shows that removing coordinated solvent molecules, 73.7% void space of the whole crystal volume (13667.3 Å$^3$ out of the 18544.0 Å$^3$ per unit cell volume) is solvent accessible (Spek et al. 'Single-crystal structure validation with the program PLATON' J. Appl. Crystallogr. 23 (2003) 7-13).

Figure 9:
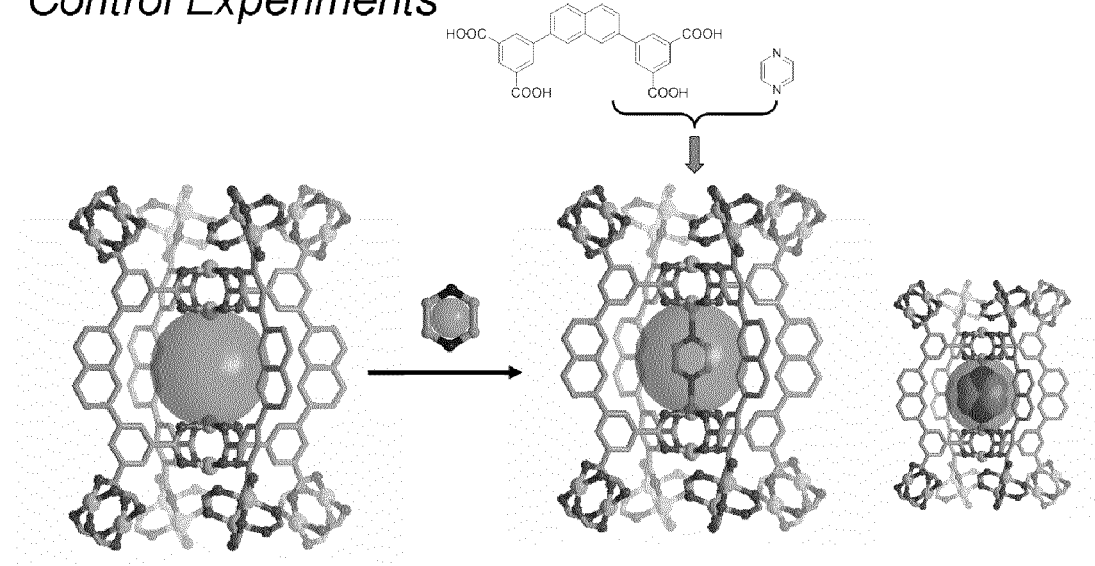
FIG. 9: Schematic showing blocking of MOF-5 by a pyrazine molecule.

Control Experiment:

To explore the "trap" effect in gas capture, MOF-5B was prepared with each "trap" being blocked by a pyrazine molecule (see FIG. 9).

4.2. $[Cu(L^4)_{1/2}(pyrazine)_{1/2}(S)]_n$ (MOF-5B, S is Coordinated Solvent Molecule) (Porous Material with Blocked Single-Molecule Traps)

Figure 8:
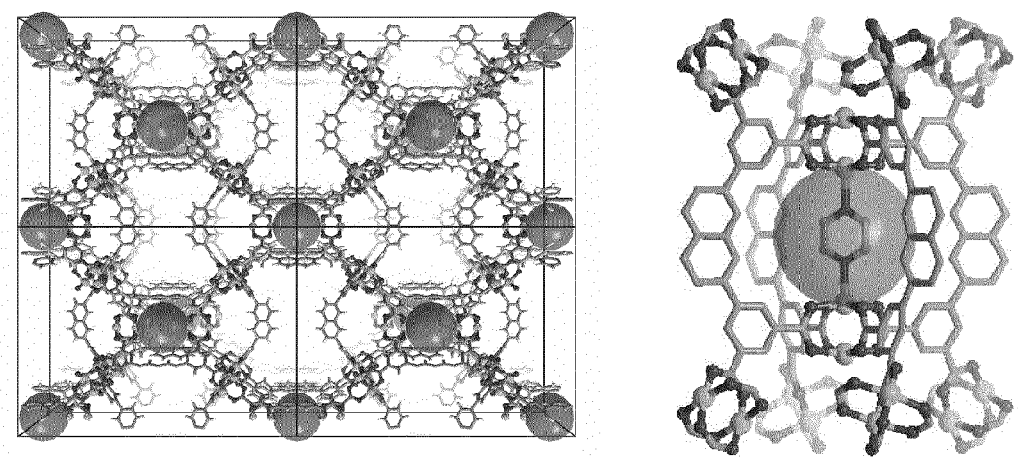
FIG. 8: Structure of MOF-5B (solvent molecules omitted for clarity)

A mixture of $H_4L^4$ (72 mg, 0.16 mmol), $Cu(NO_3)_2·2.5H_2O$ (120 mg, 0.5 mmol), pyrazine (50 mg, 0.63 mmol) 1 mL of tetrafluoroboric acid ($HBF_4$, 48% w/w aqueous solution), and 2 mL of water in 17 mL of dimethylformamide (DMF) was sealed in a 20 mL glass vial and placed in an oven at 85° C. for 48 hours. The resulting green crystals of MOF-5B were collected and washed with DMA and a little bit acetone, and then dried (yield 124 mg). FIG. 8 depicts single-crystal X-ray diffraction results.

Crystal Data:
crystalline system: orthorhombic; space group: Pnnm; a=18.152(2), b=36.438(5), c=27.432(4) Å; α=90, β=90, γ=90°; V=18144(4) Å$^3$.

4.3. $Cu_2(L^4)$(quinoxalin-6-ylmethanamine)(S) (MOF-6, S is Coordinated Solvent Molecule)

Figure 10:
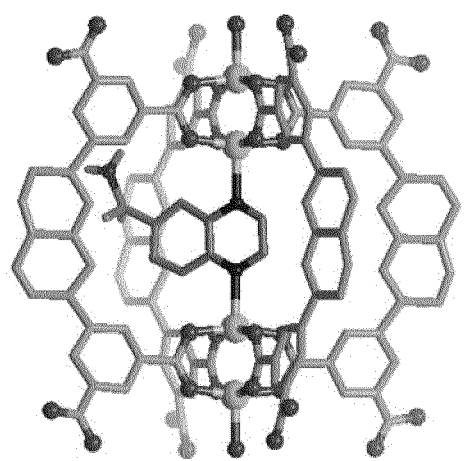
FIG. 10: Structural unit of MOF-6 showing a built-in "alkylamino" functional group.

A mixture of $H_4L^4$ (72 mg, 0.16 mmol), $Cu(NO_3)_2·2.5H_2O$ (120 mg, 0.5 mmol), quinoxalin-6-ylmethanamine (96 mg, 0.60 mmol) 1.2 mL of tetrafluoroboric acid ($HBF_4$, 48% w/w aqueous solution), and 5 mL of water in 17 mL of dimethylformamide (DMF) was sealed in a 20 mL glass vial and placed in an oven at 85° C. for 24 hours. The resulting yellow-green crystals of MOF-6 were collected and washed with DMA and a little bit acetone, and then dried (yield 120 mg). FIG. 10 depicts single-crystal X-ray diffraction results.

Crystal Data:
crystalline system: orthorhombic; space group: Pnnm; a=18.44(2), b=36.60(5), c=27.31(3) Å; α=90, β=90, γ=90°; V=18432(4) Å$^3$.

5. Gas Adsorptions in these Porous Materials

Gas adsorption measurements were performed using an ASAP 2020 volumetric adsorption analyzer. Before adsorption, the sample was activated by solvent exchange followed by degassing as detailed below. A high purity grade of gases was used throughout the adsorption experiments.

5.1. Gas Adsorptions of SMT-1 (Single-Molecule Trap)

Figure 11:
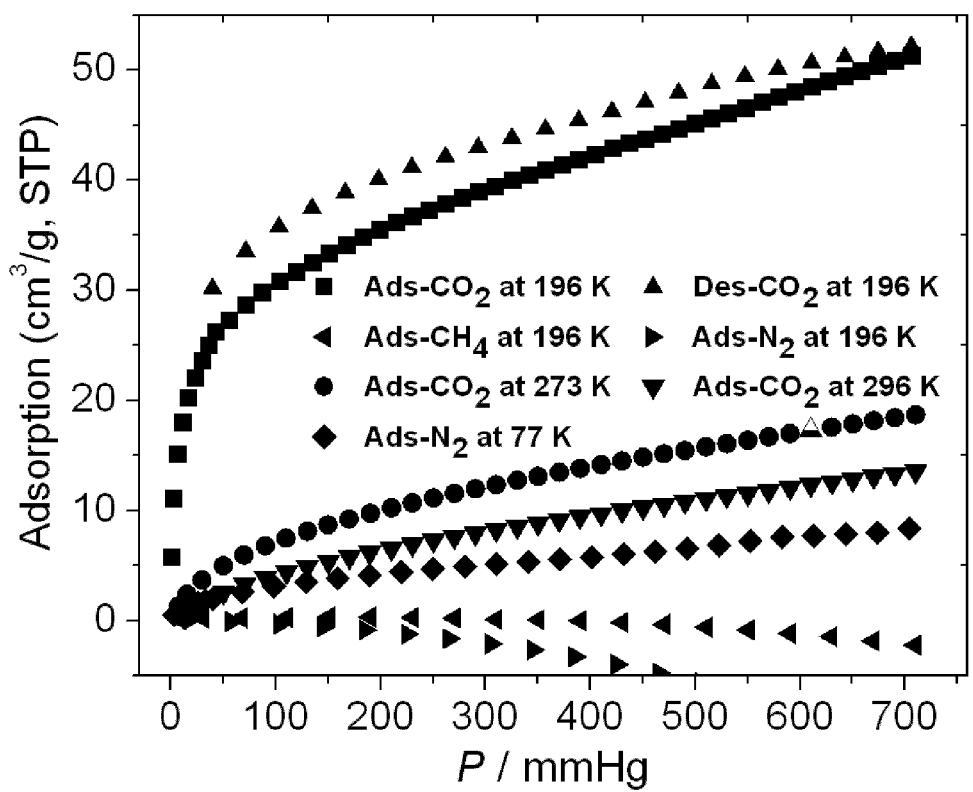
FIG. 11: Isotherm of $N_2$ and $CO_2$, and $CH_4$ with SMT-1.

Methanol-exchanged SMT-1 was further activated under high vacuum at 80° C. to give a desolvated material, SMT-1A, which was checked for gas adsorption. As shown in FIG. 11 SMT-1A shows a significant adsorption for $CO_2$ at both low and enhanced temperatures, but almost excludes $N_2$ and $CH_4$. At 196 K and 1 atm, the uptake of $CO_2$ was 52 $cm^3/g$, corresponding to about 4 $CO_2$ molecules adsorbed per SMT-1A molecule. The evaluated Langmuir surface area was 153.7 $m^2/g$ and the pore volume was 0.097 $cm^3/g$, based on the $CO_2$ adsorption data at 196 K. The adsorption capacity of $CO_2$ at 273 and 296 K was 19 and 14 $cm^3/g$, corresponding to about 1.5 and 1 $CO_2$ molecules per SMT-1A, respectively. The de-solvated SMT-1A sample was still crystalline as confirmed by powder XRD, but the diffraction peaks derivate from those of DMA-solvated (SMT-1). This situation is different from several MOP materials reported, which usually became amorphous after removal of the solvent molecules.

5.2. Gas Adsorptions of SMT-4 (Single-Molecule Trap)

5.2.1. Activation of SMT-4

Figure 12:
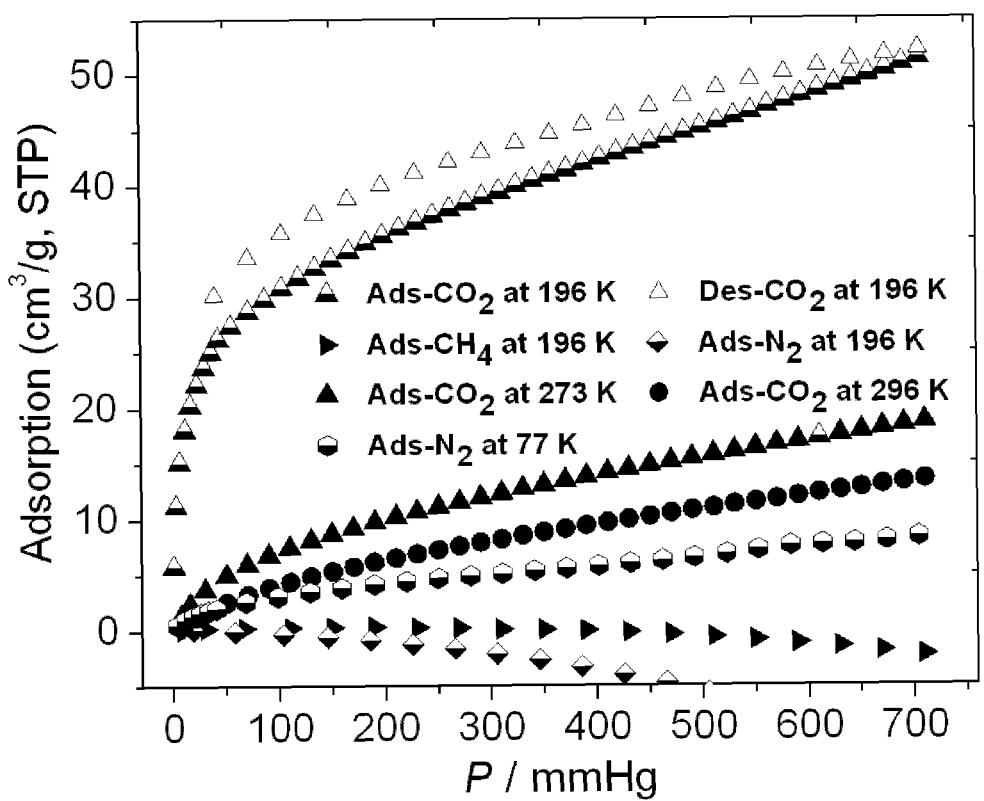
FIG. 12: Isotherm of $N_2$ and $CO_2$, and $CH_4$ with material SMT-4.

An as-synthesized sample of SMT-4 (about 100 mg) was soaked in methanol for 24 h, and the extract was discarded. Fresh methanol was subsequently added, and the sample was allowed to stay in methanol for an additional 24 h before methanol was removed. After decanting the methanol extract, the sample was dried under a dynamic vacuum ($<10^{-3}$ Torr) at room temperature for 1 hour. Before adsorption measurement, the sample was further activated using the "outgas" function of the adsorption analyzer for 200 minutes at 100° C. Finally, 85 mg sample was used in gas adsorption measurement. After activation, the sample became amorphous. Isotherms of $N_2$ and $CO_2$, and $CH_4$ are shown in FIG. 12.

It is clear that only $CO_2$ was adsorbed by this single-molecule trap material.

5.3. Gas Adsorptions of MOF-5 (Porous Material with Built-in Single-Molecule Traps) and MOF-5B (Porous Material with Blocked Single-Molecule Traps)

5.3.1. Activation of MOF-5 and MOF-5B

MOF-5 and MOF-5B were activated as follows: an as-synthesized sample (about 110 mg) was soaked in methanol for 24 h, and the extract was discarded. Fresh methanol was subsequently added, and the sample was allowed to stay in methanol for an additional 24 h before methanol was removed. This procedure was repeated 6 times. After decanting the methanol, dichloromethane was used. The same procedure as that using methanol was repeated 6 times. After decanting the dichloromethane extract, the sample was dried under a dynamic vacuum ($<10^{-3}$ Torr) at room temperature for 2 hours. Before adsorption measurement, the sample was further activated using the "outgas" function of the adsorption analyzer for 800 minutes at 80° C. The structure remained porous as confirmed by PXRD.

Figure 13A:
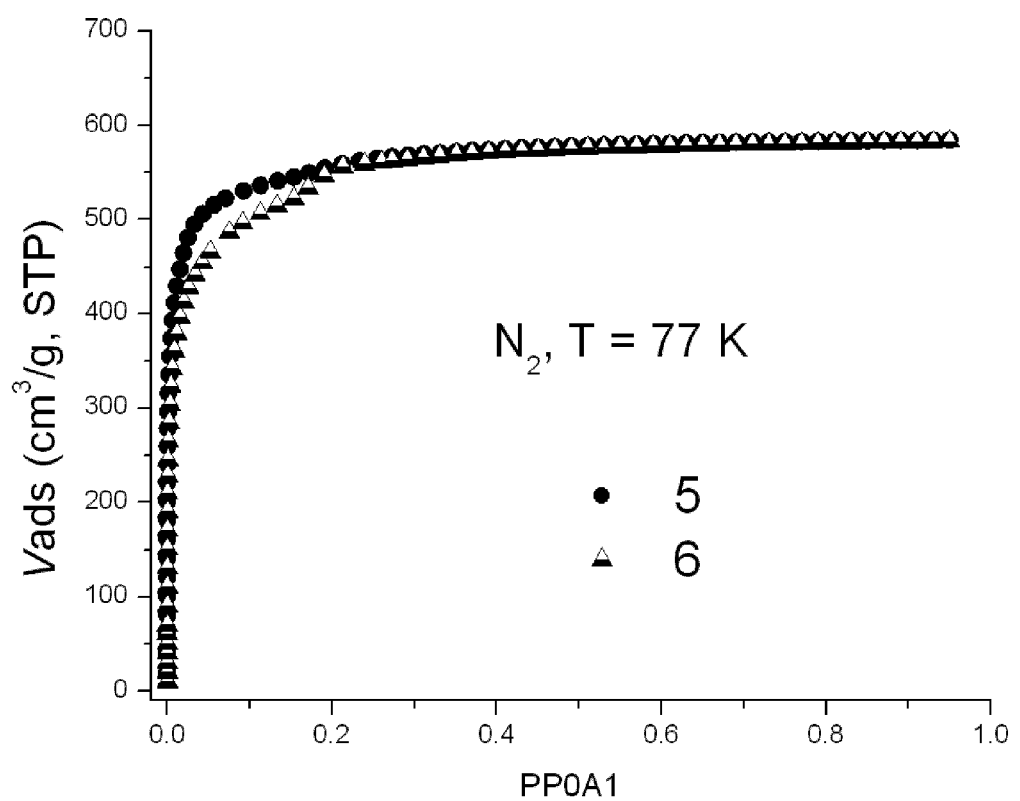
FIG. 13A: Isotherm of $N_2$ with materials MOF-5 and MOF-5B.
Figure 13B:
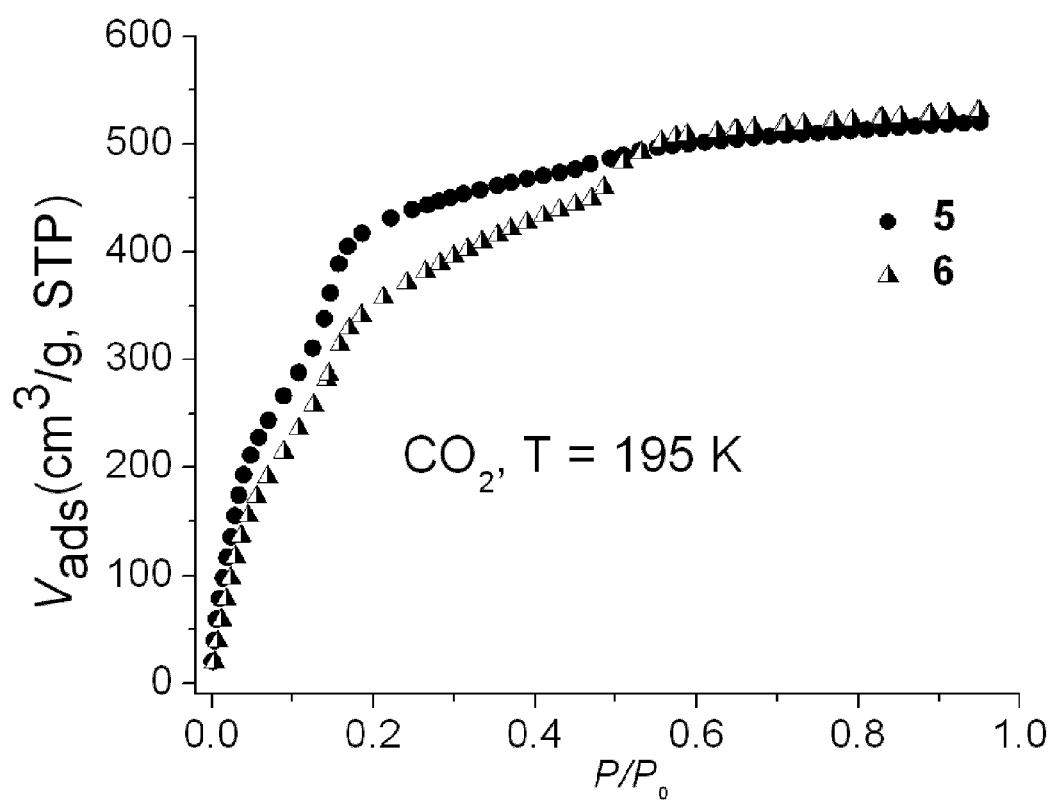
FIG. 13B: Isotherm of $CO_2$ with materials MOF-5 and MOF-5B.
Figure 13C:
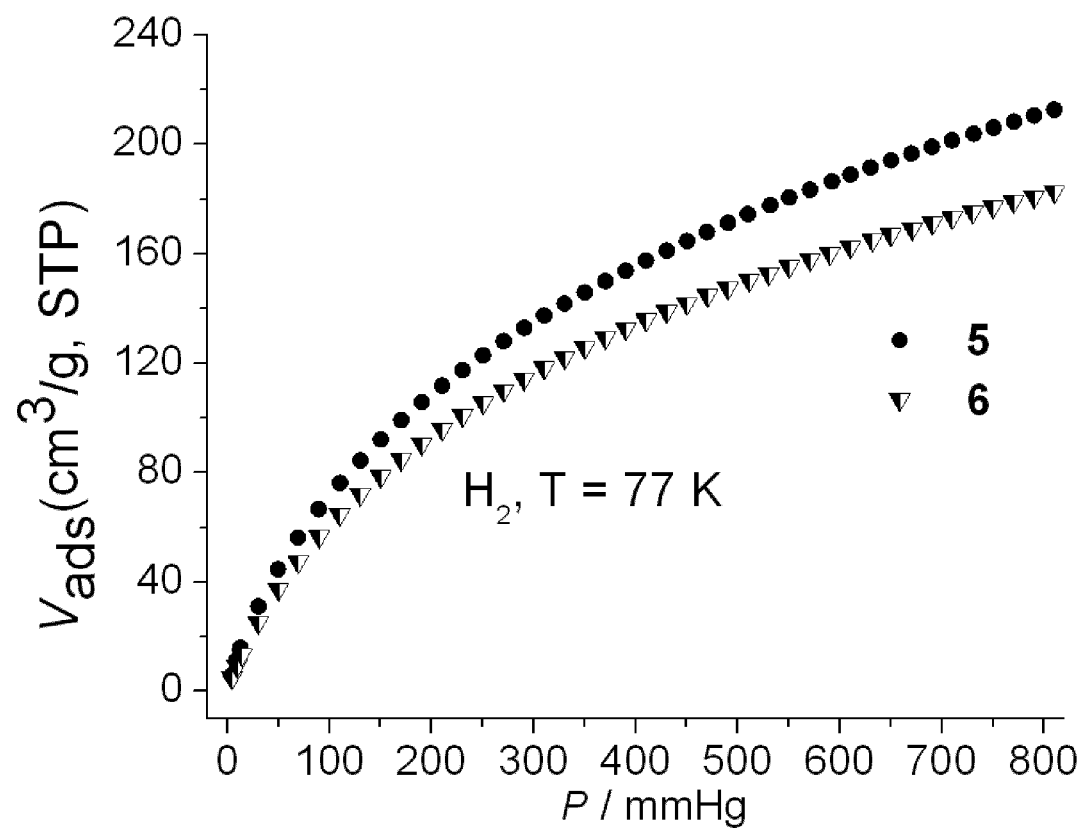
FIG. 13C: Isotherm of $H_2$ with materials MOF-5 and MOF-5B.

Finally, about 80 mg sample was used in gas adsorption measurement in each case. Isotherms of $N_2$ and $CO_2$, and $H_2$ are shown in FIGS. 13A-13C.

5.3.2. Gas Adsorptions of MOF-5

The $N_2$ and Ar adsorption isotherms at 77 and 87 K (not shown) further revealed its permanent porosity, with BET and Langmuir surface areas of 3308 and 3845 $m^2/g$, respectively based on the $N_2$ adsorption data (calculated from the first step adsorption isotherm). A two-step adsorption was observed in $N_2$ and Ar isotherms, which can be explained by the co-existence of both meso- and micro-porous traps in the structure. MOF-5 takes up different amounts of $CO_2$ (160 and 94 $cm^3/g$), $CH_4$ (33 and 18 $cm^3/g$), and $N_2$ (2.6 and 2.1 $cm^3/g$) at 273 and 298 K and 1 atm, respectively. These observed selective adsorptions of $CO_2$ over $CH_4$ and $N_2$ can be attributed to the much stronger interactions of $CO_2$ molecule with the adsorbent surface compared to those of another two gases.

5.3.3. Gas Adsorptions of MOF-5B

Blocking the cavities of SMTs in MOF-5 gives MOF-5B $[Cu(L^4)_{1/2}(pyrazine)_{1/2}(S)]_n$, in which the trap cavities are occupied by pyrazine molecules through coordinating to two copper sites. MOF-5B was synthesized by a one-pot reaction of $H_4L^3$, pyrazine, and $Cu(NO_3)_2.2.5H_2O$ under similar conditions to that for MOF-5. Its structure is similar to that of MOF-5 with the only difference being the blocked SMTs as mentioned above. The structure contains the pore accessible volume of 72.6% (13530.0 out of the 18646.0 $Å^3$ per unit cell volume) after removed coordinated solvent molecules are removed. The permanent porosity of the MOF-5B desolvated material, was revealed by the $N_2$ and Ar adsorption. The evaluated BET and Langmuir surface areas were 3,042 and 3,799 $m^2/g$, respectively based on the $N_2$ adsorption data. Similar to that of MOF-5, a two-step adsorption for $N_2$ and Ar, and different amounts of uptakes for $CO_2$ (119 and 70 $cm^3/g$), $CH_4$ (27 and 15 $cm^3/g$), and $N_2$ (2.4 and 1.8 $cm^3/g$) at 273 and 298 K and 1 atm, respectively were observed. Clearly, compared to MOF-5, MOF-5B shows a lower adsorption capacity towards these gases at 273 and 296 K due to blocking of the SMT cavities. At 195 K, both MOFs showed almost the same $CO_2$ uptake of about 850 $cm^3/g$ at 1 atm; however MOF-5 has a significantly enhanced $CO_2$ compared with MOF-5B at a low pressure (lower than 0.15 $P/P_0$). This higher adsorption at low pressure should be attributed to the contribution from SMTs in MOF-5. For MOF-5B, the calculated Henry's law selectivities for $CO_2$ over $CH_4$ and $N_2$ are 6.1 and 49.4 at 273 K, and 5.0 and 12.6 at 296 K, respectively, and IAST selectivities are 16.5 and 18.5 at 273 K and 1 bar, and 12.3 and 14.6 at 296 K, for 15/85 and 50/50 $CO_2/N_2$ mixtures, respectively. The related values for a 50/50 $CO_2/CH_4$ mixture are 6.6 and 5.8 at 273 K and 1 bar and at 296 K and 1 bar, respectively. All these evaluated selectivities in MOF-5B are lower than those of MOF-5, indicating that the SMTs in the former have a great effect on the selective adsorption of $CO_2$ over $CH_4$ and $N_2$. The zero coverage heat of adsorption of $CO_2$ in MOF-5B is -26 kJ/mol, again lower than that in MOF-5. In addition, it was also noted that MOF-5 has a higher $H_2$ uptake than that of MOF-5B at 77 and 87 K, respectively, but both show close adsorption enthalpies This control experiment therefore shows that the SMTs have a significant influence on the $CO_2$ selective adsorption.

From these adsorption results, the following conclusions may be made:

1) MOF-5 and MOF-5B presented almost identical $N_2$ uptake. This can be explained as that the kinetic diameter of $N_2$ is larger than the size of "traps", thus, blocking "trap" does not have an effect on $N_2$ uptake.

2) At low pressure, $CO_2$ uptake in MOF-5 is obviously higher than that in MOF-5B. This is a "trap" effect; the kinetic diameter of $CO_2$ is smaller than the size of traps in MOF-5, which allow $CO_2$ adsorption. (MOF-5B was configured just for $CO_2$ capture).

3) $H_2$ has a much smaller kinetic diameter than that of $CO_2$, thus MOF-5 presented higher $H_2$ adsorption than that of MOF-5B, in which "traps" were blocked. Clearly, the "trap" effect has been confirmed by this control experiment.

6. Synthesis of $[Cu(tzc)(dpp)_{0.5}]_n \cdot 1.5H_2O$ MOF-7 (tzc=tetrazolate-5-carboxylate, dpp=1,3-di(4-pyridyl)propane)

Microcrystalline bulk material was prepared by a reaction of $Cu(OAc)_2$ (363.2 mg, 2.0 mmol), sodium ethyl ester tetrazolate-5-carboxylate (NaEttzc, 328.2 mg, 2.0 mmol), dpp (198.2 mg, 1.0 mmol) in 15 mL $H_2O$. After stirring this mixture at 150° C. for 1 day, the resultant blue precipitate was filtered, washed with $H_2O$, EtOH and $Et_2O$, and dried in air. Yield: 574 mg (95%). Blue crystalline plates for single crystal X-ray diffraction studies were isolated from the reaction of a mixture containing $Cu(OAc)_2$ (36.3 mg, 0.2 mmol), NaEttzc (32.8 mg, 0.2 mmol), dpp (19.8 mg, 0.1 mmol) and 3 mL $H_2O$ at 100° C. for 4 days. The structure of MOF-7 was determined by single-crystal X-ray diffraction (FIGS. 14, 15).

Figure 14:
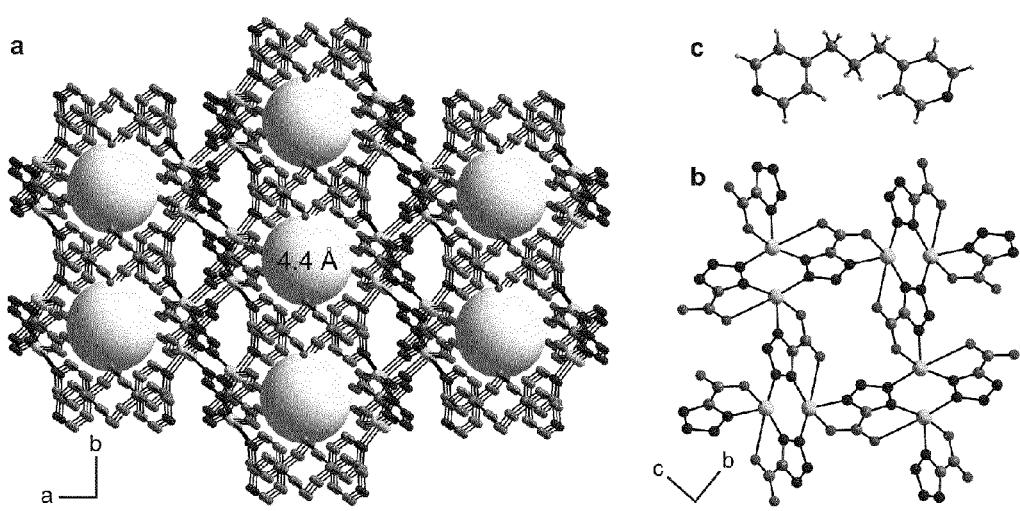
FIG. 14: Crystal structure of MOF-7.
Figure 15:
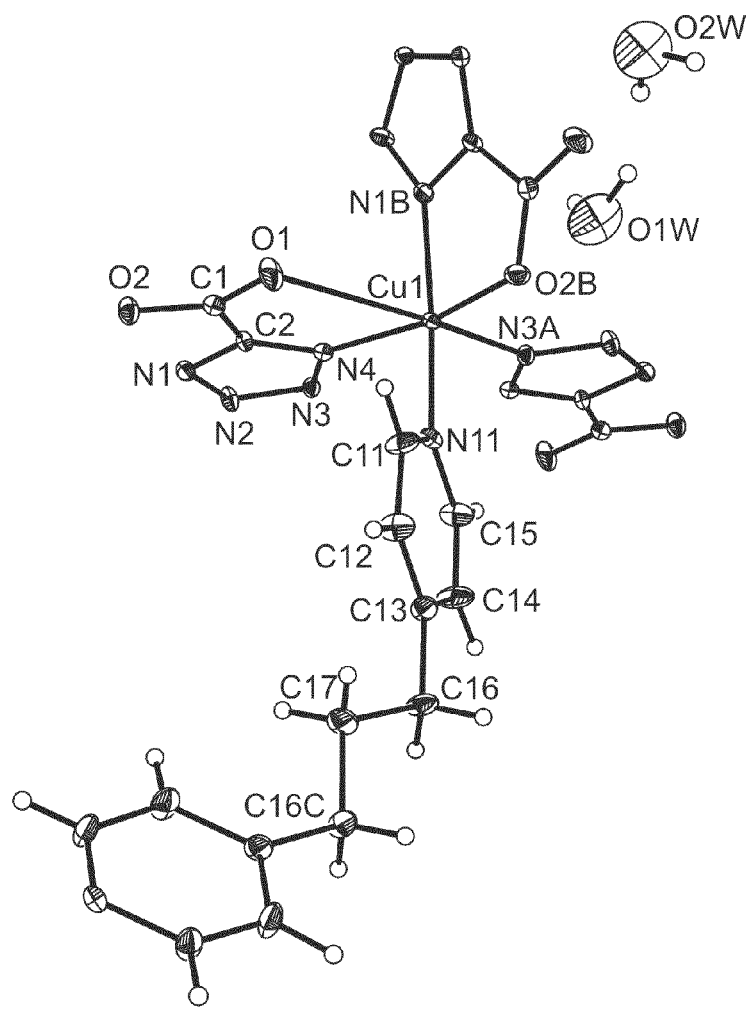
FIG. 15: Molecular structure of MOF-7.

From FIG. 14 it can be seen that the framework organizing these traps in space, $[Cu(tzc)(dpp)_{0.5}]_n \cdot 1.5H_2O$, has proper Cu...Cu distances in the direction of the b axis to form $CO_2$ pockets, controlled by $\mu_3$-bridging tzc ligands forming layers in the b-c plane (FIG. 14b). The flexible N-donor linker dpp (FIG. 14c) provides the strong inter-layer bonds that connect these layers into a 3D network forming 1D pores along the c axis with the center of the pores located on a center of inversion (FIG. 14a). dpp therefore ensures the correct inter-sheet distance to accommodate exactly one $CO_2$ molecule, while the flexibility of the linking propane chain unexpectedly allowed an advantageous elastic trapping effect to be achieved.

Upon $CO_2$ adsorption, the elastic nature of the pore leads to a unique, site-selective single-molecule trapping of the gas molecules. The pore form continues to change to fit the $CO_2$ (pore distances of 9.01(1)/8.444(1)×13.92(1)/13.54(3) Å), by fitting exactly one gas molecule per pore or rather four molecules per unit cell. The $CO_2$ molecules within the plane of the pore are located on an inversion center at the center of the pore with distances between the $CO_2$ and the pore surface in the range of 2.63(4)-4.501(1)/2.61(6)-4.28(5) Å. Thus, no strong interactions can be found suggesting only moderate van der Waals interactions of the gas molecules with the framework, exactly as is expected from molecules in a purely physically adsorbed state. These multipoint bonded $CO_2$ molecules offer ideal conditions for a reversible $CO_2$ sorption process. The C—C distance of $CO_2$ molecules is 4.64(4)/4.63(4) Å.

$[Cu(tzc)(dpp)_{0.5}]_n \cdot 1.5H_2O$ crystallizes in the centrosymmetric monoclinic space group C2/c with eight formula units in the unit cell. The asymmetric unit consists of one dpp ligand and one non-coordinating water molecule located around a 2-fold rotation axis. Furthermore, one Cu(II) cation, one tzc ligand and one non-coordinating water molecule are located in crystallographically independent general positions. In the crystal structure each Cu(II) cation is coordinated by three symmetry related tzc ligands and one dpp ligand in an octahedral geometry (FIG. 15). The $CuN_4O_2$ octahedron is markedly stretched with one long Cu—$O_{tzc}$ and Cu—$N_{tzc}$ distance of 2.248(5) and 2.913(2) Å and four short Cu—$O_{tzc}$/$N_{tzc}$/$Na_{dpp}$ distances in the range of 1.986(5)-2.022(5) Å, whereas the angles around the metal cations range between 82.30(19)-99.95(19) and 163.4(2)-166.8(2)°. Each tzc ligand connects three Cu(II) cations through two carboxylate oxygen atoms and three nitrogen atoms to give a $\mu_3$-N4,O1:N1, O2:N3 bridging mode. Double N—N bridges of two opposite tzc ligands link adjacent Cu(II) cations forming an almost planar six-membered ring with a torsion angle of Cu1-N3-N4-Cu1A of 7.7(8)° and with a Cu1-Cu1A distance in this dimeric $Cu_2(N-N)_2$ moiety of 4.173(2) Å. These units are $\mu_3$-tzc bridged into layers along the crystallographic b-c plane (FIG. 14b), which are further connected by the flexible N-donor linker dpp (FIG. 14c) into a 3D network forming 1D pores along the crystallographic c-axis with the center of the pores located on a center of inversion (FIG. 14a). The environment of the pores is formed by exposed carboxylate groups and the dpp ligand with shortest O—O distances of opposite carboxylates being 13.01(1) Å and a C—C distance of the middle C-atom of opposite dpp ligands being 9.33(2) Å. Non-coordinating water molecules occupy the pores (FIG. 18b: bottom) stabilized by strong hydrogen bonding.

Figure 18:
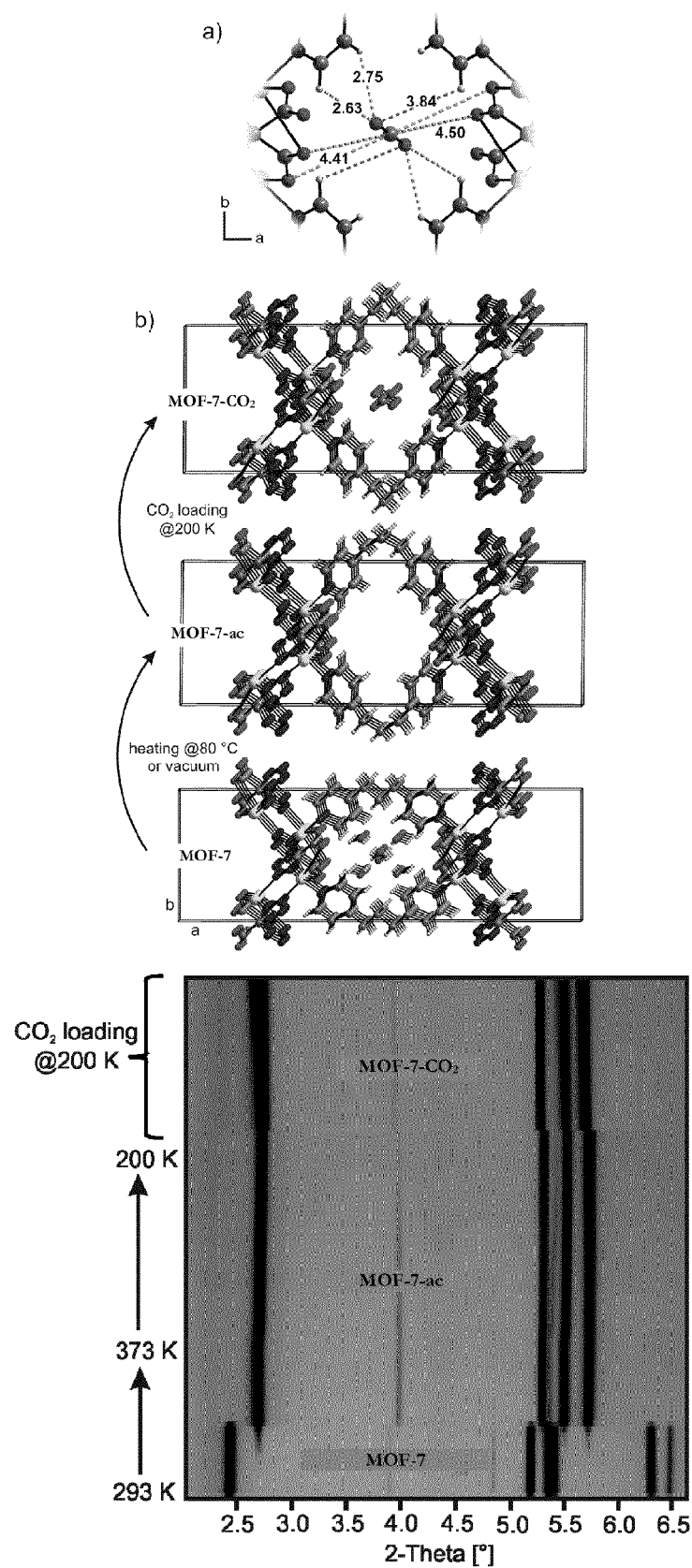
FIG. 18: Structural changes of MOF-7 upon activation and $CO_2$ adsorption.

In the as-synthesized structure, non-coordinating water molecules occupy the pores (FIG. 18b: bottom) and are stabilized by strong hydrogen bonding. The water molecules of the precursor compound can be easily removed by either heating or applying vacuum leading to the activated phase $[Cu(tzc)(dpp)_{0.5}]_n$ (FIG. 14a, FIG. 18b: middle). This activation process is accompanied by a phase transition keeping the same space group (C2/c), almost the same unit cell length parameters, but a dramatic change in the unit cell angle β, from 92.657(10)° to 116.087(4)° in the activated product. The crystal structure of desolvated MOF-7 was solved from in situ synchrotron X-ray powder diffraction (XRPD) patterns and refined by the Rietveld method. Due to the elastic nature of the dpp ligand, the pores opened up to where the largest vdW sphere has a diameter of 4.4 Å, which can be used to fit exactly one gas molecule per pore (desolvated MOF-7 is stable up to 218° C., which meets the temperature requirements for physical sorbents in a flue gas separation process. Chemical stability tests show that MOF-7 is stable after stirring in HCl (pH=3) and NaOH (pH=12) and boiling in water for 7 days, further confirming the substantially stronger inter-sheet stability afforded by the nitrogen-copper bonds.

6.1. Activation of MOF-7

It has been shown that this material can lose water molecules from its pores by heating it up to 80° C. in helium stream or by simply evacuating room temperature for 5 minutes. These activation conditions are extremely simple compared to typical solvent exchange and activation procedures necessary for most other MOF materials. However both of these activation methods potentially use substantial amounts of energy on the large scale required for flue gas applications. To test a completely new activation method, a gas cell at 1-BM line at Advanced Photon Source at Argonne National Laboratory was used. The experiment comprised packing the cell with as-synthesized MOF-7 and flowing a stream of anhydrous $CO_2$ at 40° C. though the in situ flow-cell (packed bed of MOF-7 powder). On each side of the capillary two heating electric-furnace elements were added. To control the temperature of the sample, the miniature thermocouple was placed inside the capillary.

Figure 16:
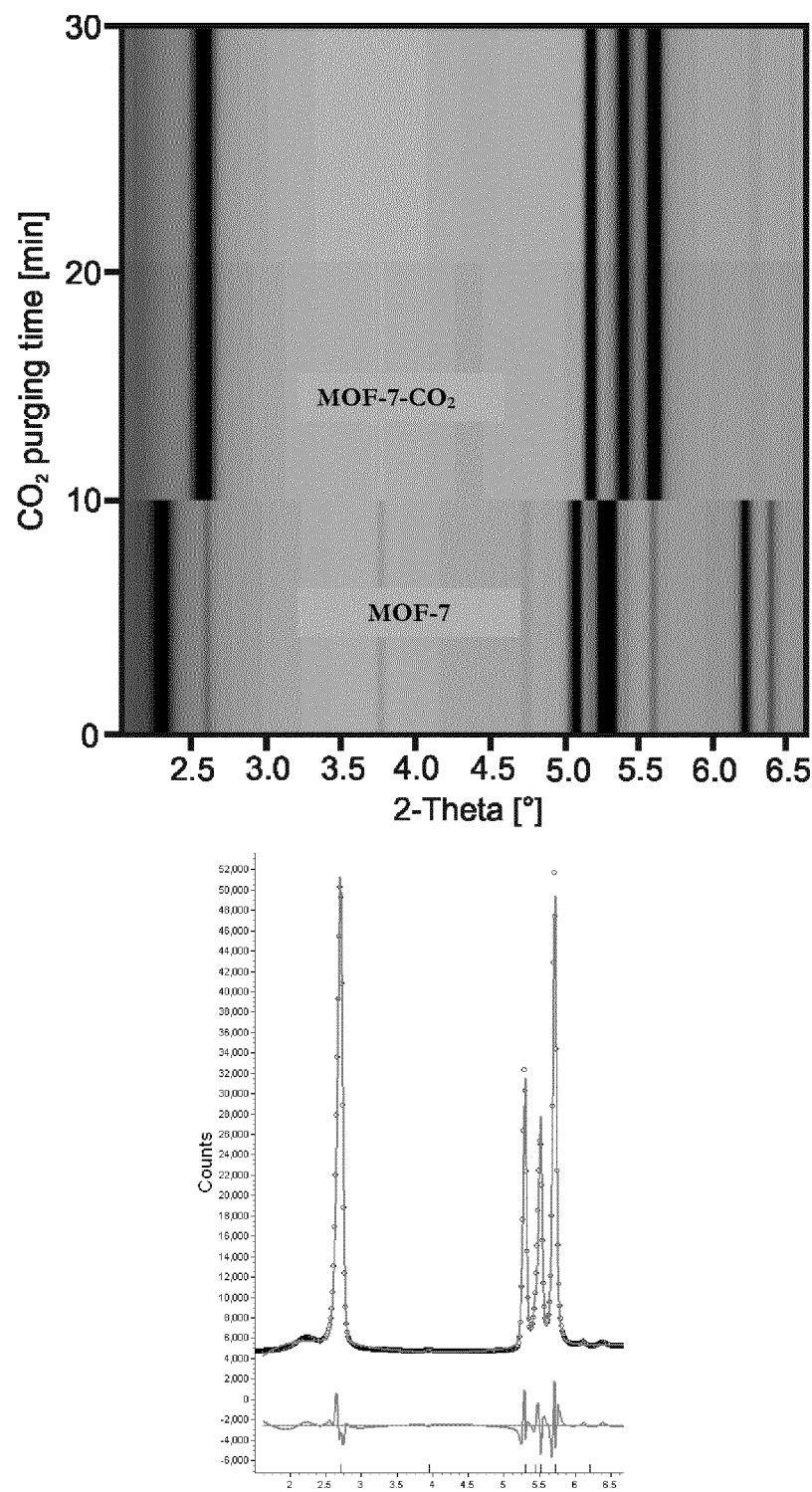
FIG. 16: XRPD patterns of MOF-7 activation experiment.
Figure 19:
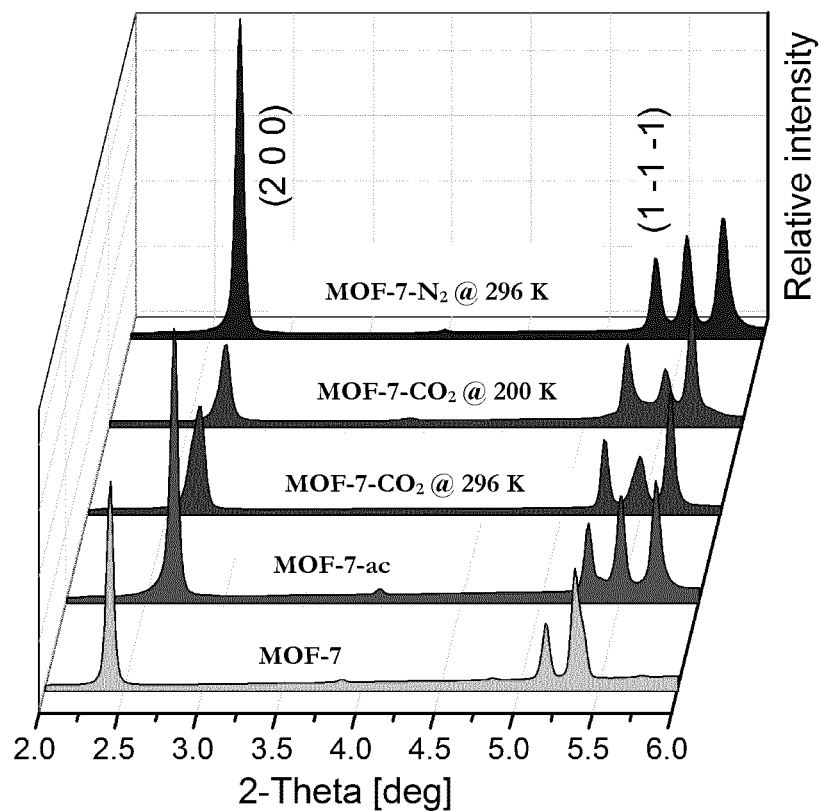
FIG. 19: Gas-loading of MOF-7.

During the experiment a sample of MOF-7 was under a continuous flow of $CO_2$ and the temperature was slowly raised to 40° C. After which the temperature was held constant and powder diffraction patterns were recorded every 1 min for 50 min. The results of the experiment are presented in FIG. 16 (top). We can clearly see that activation of MOF-7 happens after only 10 min in the warm stream of $CO_2$. The FIG. 16 (bottom) powder pattern was taken and refined by typical methods and as can be seen in matches well with the $CO_2$-loaded phase of MOF-7. This is further confirmed by comparing the intensity distribution of first four major diffraction peaks with our previous results (FIG. 19). From this it can be concluded that the resulting phase is void of all water molecules in the pores and that they have in fact been replaced with molecules of carbon dioxide.

This makes the process of MOF-7 activation very simple and low in energy consumption. This result is also very important from a fundamental and practical standpoint as solvent water in the pores of MOF molecules were replaced by gas molecules without the application of high temperatures or vacuum.

7. Evaluation of Selective Adsorption

To show that MOF-7 can selectively adsorb $CO_2$ over $N_2$ in a practical setting, it was evaluated from three mutually independent, well-established techniques: single component gas adsorption isotherms, binary gas adsorption simulations, and crystallographic determination of the adsorbed gas, the results of which all confirm high selectivity.

8. Single-Component Gas Isotherms

Figure 17:
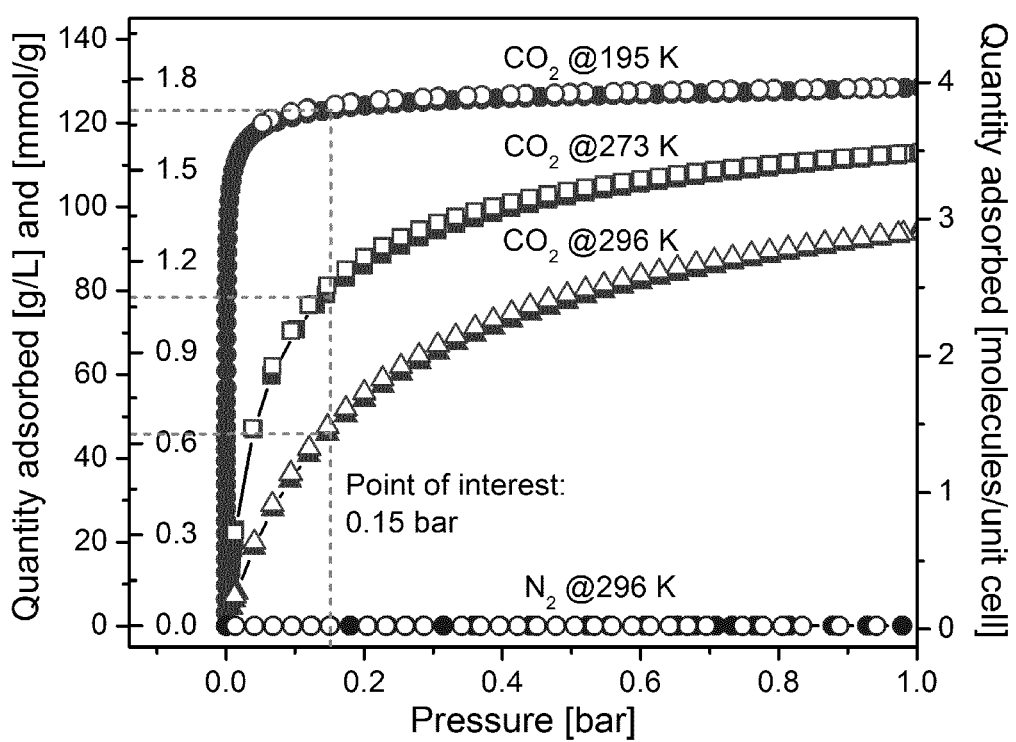
FIG. 17: Isotherm of $N_2$ and $CO_2$ with material MOF-7.

The first technique is using experimental single component gas isotherms to examine loading capacities of $CO_2$ and $N_2$ at various temperatures (FIG. 17). The completeness of the activation procedure is clearly shown by the $CO_2$ uptake at 195 K, which reaches full saturation of 4 molecules per unit cell (1.78 mmol/g) at 1 bar. Simulated single gas isotherms are in excellent agreement with these experimental observations. An additional consideration that must be taken into account is the volumetric storage capacities, as the volume of the adsorbent plays a significant role in industrial scale applications (Ciferno et al. 'Technology Integration Challenges' Chem. Eng. Prog. 107, 34-44 (2011). The exceptionally high density of desolvated MOF-7 (1.64 g/mL) compared to other MOFs leads to a high uptake capacity of 129 g/L. More importantly, the material retains 75% of its uptake capacity under ambient conditions.

8.1. Quantification of Adsorption Affinities

To quantify the adsorption affinities, we used two common methods, fitting experimental gas isotherms using both the virial and Langmuir equations and calculating zero coverage heats of adsorption (−38 kJ/mol and −49 kJ/mol, respectively). These values fall well within the range of what is considered to be an ideal adsorption enthalpy for $CO_2$ scrubbing from flue gas. Adsorption enthalpies that are too low translate to low selectivities while higher enthalpies will raise regeneration costs because of the energy input required for the reverse process. The high energy requirement required for the regeneration of aqueous amine solutions stems from the high adsorption enthalpies of chemisorption (−50 to −100 kJ/mol) and the high heat capacity of the aqueous amine solution (approx. 3.5 $J \cdot g^{-1} \cdot K^{-1}$ vs. MOF-7, 0.9 $J \cdot g^{-1} \cdot K^{-1}$). Because of their modular design, MOFs have been tuned to selectively capture $CO_2$ through the incorporation of unsaturated metal centers or polar functional groups (Llewellyn, P et al. 'High uptakes of $CO_2$ and $CH_4$ in Mesoporous Metal-Organic Frameworks MIL-100 and MIL-101. Langmuir 24, 7245-7250 (2008); Mason et al. 'Evaluating metal-organic frameworks for post-combustion carbon dioxide capture via temperature swing adsorption. Energy Environ. Sci. 4, 3030-3040 (2011); McDonald, T et al. 'Enhanced carbon dioxide capture upon incorporation of N,N'-dimethylethylenediamine in the metal-organic framework CuBTTri. Chem. Sci. 2, 2022-2028 (2011).

The difference in the approach described herein is that no high enthalpy adsorption interactions are used. Instead, a polar pocket was created that traps $CO_2$ and excludes other gas molecules; the moderate heat of adsorption results from a combination of polar pore surface and pore size. By controlling guest-framework interactions a material was synthesized that requires very little energy to regenerate, yet has extremely high selectivity for $CO_2$. The precise configuration of the $CO_2$ trap thus leads to a remarkably high adsorption enthalpy for a purely physisorptive material.

9. Binary Gas Adsorption Simulations

The second technique, annealing simulations, shows that both gas molecules compete for the adsorption site at the center of the pocket leading to selectivity values of 260 (50:50) and 205 (15:85) for binary $CO_2/N_2$ mixtures at 296 K and 1 bar according to our Grand-Canonical Monte Carlo (GCMC) simulations.

10. Crystallographic Determination of Adsorbed Gas

The crystal structure of the $CO_2$ loaded phase (MOF-7-$CO_2$) was solved from in situ synchrotron XRPD patterns and refined the data by the Rietveld method (FIG. 18a: top and FIG. 18c, see Methods). The transition from as-synthesized to activated to gas loaded phases can clearly be seen in the 'top view' of the powder patterns (FIG. 18b). We used this, the third technique, to give us insights to the $CO_2$ trapping mechanism. The crystallographic determination of $CO_2$ at the center of the pore is confirmed by annealing simulations and DFT calculations, which show multi-point $CO_2$-framework interactions. The high selectivity can be explained by the special adsorption properties of MOF-7 where all adsorption sites are shared by $CO_2$ and $N_2$: $CO_2$ is heavily favored in competition due to its stronger interactions with the framework.

The activation and gas loading process can be followed by only a few reflections as shown in FIG. 19. Upon activation, the (200) reflection is shifted to higher 2-Theta values (~2.7°) and the doublet in the 5-6° 2-Theta range splits into a triplet. Upon gas loading, the intensities become relevant: Depending on the gas loading, the relative intensities of the (200) and the (1-1-1) at ~5.3° reflection change. The higher the gas uptake, the less intense the (200) and the more intense the (1-1-1) reflection, which is evident when comparing the $CO_2$ patterns at 296 and 200 K. The nearly identical patterns of desolvated MOF-7 and the $N_2$ loaded phase again emphasize the disparity between $N_2$- and $CO_2$-frameworks interactions. As is to be expected from changes in reflection position and intensity, minor changes in unit cell parameters and atom-atom bond distances/angles are also observed.

11. Flue Gas Simulations

Stability tests have been performed on MOF-7 in a simulated flue gas environment. 20 cc to 30 cc of MOF-7 was loaded into the cell (customized tube) and a simulated flue gas stream was blown through to saturate the sorbent. The flue gas stream consisted of 15% $CO_2$, 84% $N_2$ and was saturated ($H_2O$). $SO_x$ and $NO_R$, less than one percent of the stream, exceeded ARPA-E (US Department of Energy) requirements of 20 PPM $SO_x$ and to PPM $NO_x$. Desorption was tested at low temperature, 40° C., with helium or argon, and also at a higher temperature of 60° C. 30 cycles (adsorption and desorption) were tested for each MOF-7 bed to determine $CO_2$ capacity change (measured by mass spectrometry).

While the preferred embodiment of the invention has been illustrated and described, it will be appreciated that various changes can be made therein without departing from the spirit and scope of the invention.

The invention claimed is:
1. A porous material comprising (i) a single pore having a single pore size or (ii) a plurality of pores having an average pore size, wherein the single pore size or the average pore size is proportioned to accommodate a single gas molecule to the exclusion of additional gas molecules;
   wherein the single gas molecule is positioned between at least two metal ion dimers in a pore of the material, wherein each dimer comprises an outer metal ion and an inner metal ion, wherein each inner metal ion partici- pates in binding the single gas molecule, and wherein the outer metal ion and the inner metal ion are the same; and wherein (a) each metal ion dimer is bonded by four bis(monodentate) ligands, and at least one of the bis(monodentate) ligands is selected from a compound of formula (I) or (II):

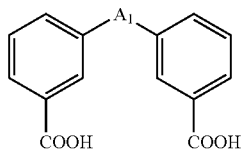
(I)

wherein $A_1$ is selected from the group consisting of naphthalenyl, quinolinyl, naphthyridinyl, anthracenyl, and acridinyl;

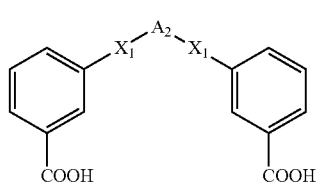
(II)

wherein $A_2$ is selected from the group consisting of phenyl, pyridinyl, naphthalenyl, naphthyridinyl, and acridinyl, and $X_1$ is selected from the group consisting of ethynyl,

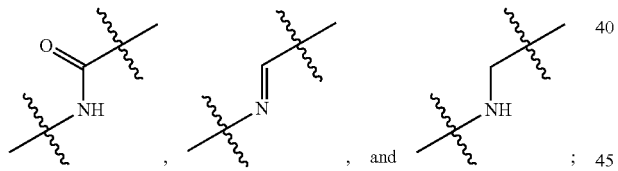

; or (b) each metal ion dimer is bonded by four tetra(monodentate) ligands, and at least one of the tetra(monodentate) ligands is selected from a compound of formula (V) or (VI):

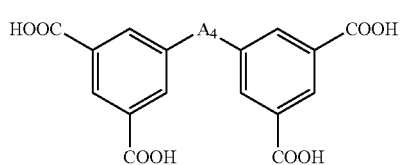
(V)

wherein $A_4$ is selected from the group consisting of pyridinyl, naphthalenyl, quinolinyl, naphthpyridinyl, anthracenyl, and acridinyl;

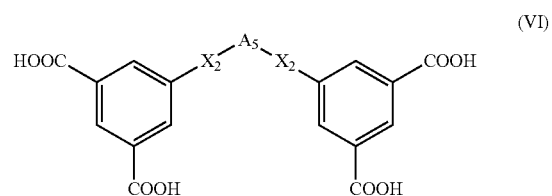
(VI)

wherein $A_5$ is selected from the group consisting of phenyl, pyridinyl, naphthalenyl, naphthpyridinyl, and acridinyl, and $X_2$ is selected from the group consisting of ethynyl,

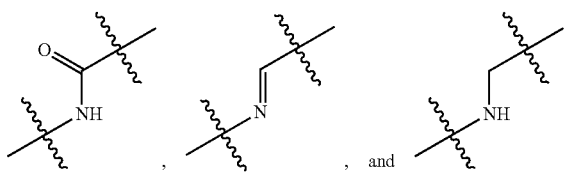

, and

2. The porous material of claim 1, wherein the porous material is synthetic.

3. The porous material of claim 1, wherein the material can be activated to coordinate a solvent molecule in a pore.

4. The porous material of claim 1, wherein the gas molecule is selected from $CO_2$, $H_2$, $N_2$, CO, $O_2$, $CH_4$, $C_2H_4$, $SO_2$, $H_2S$, $CS_2$, $NH_3$, NO, and $C_3H_6$, or a combination thereof.

5. The porous material of claim 1, wherein each metal ion of each dimer is selected from the group consisting of Cu, Ru, Zn, Co, Rh and Mo.

6. The porous material of claim 5, wherein each metal ion of each dimer is Cu(II) or Ru(II).

7. The porous material of claim 1, wherein the material comprises a single pore, and wherein the single pore comprises a single gas molecule.

8. The porous material of claim 1, wherein the compound of formula (I) is selected from the following:

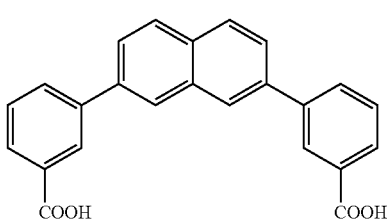
A

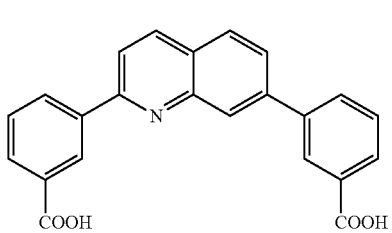
B

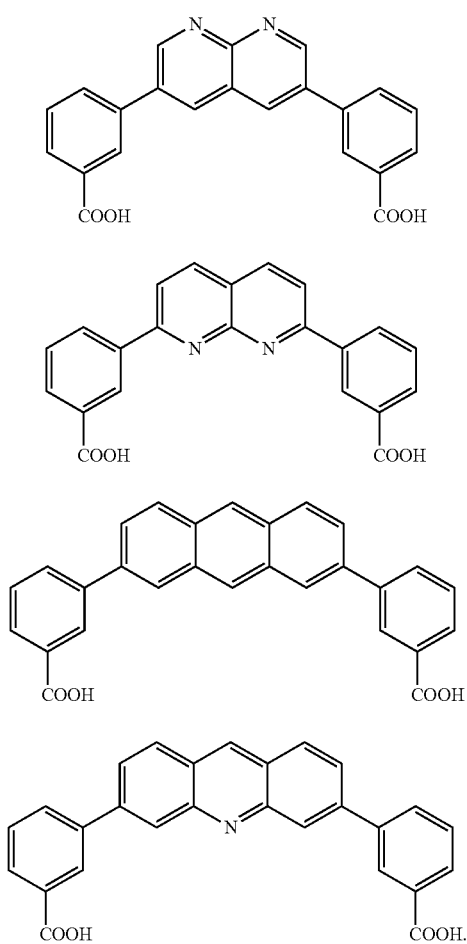
9. The porous material of claim 1, wherein the compound of formula (II) is selected from the following:
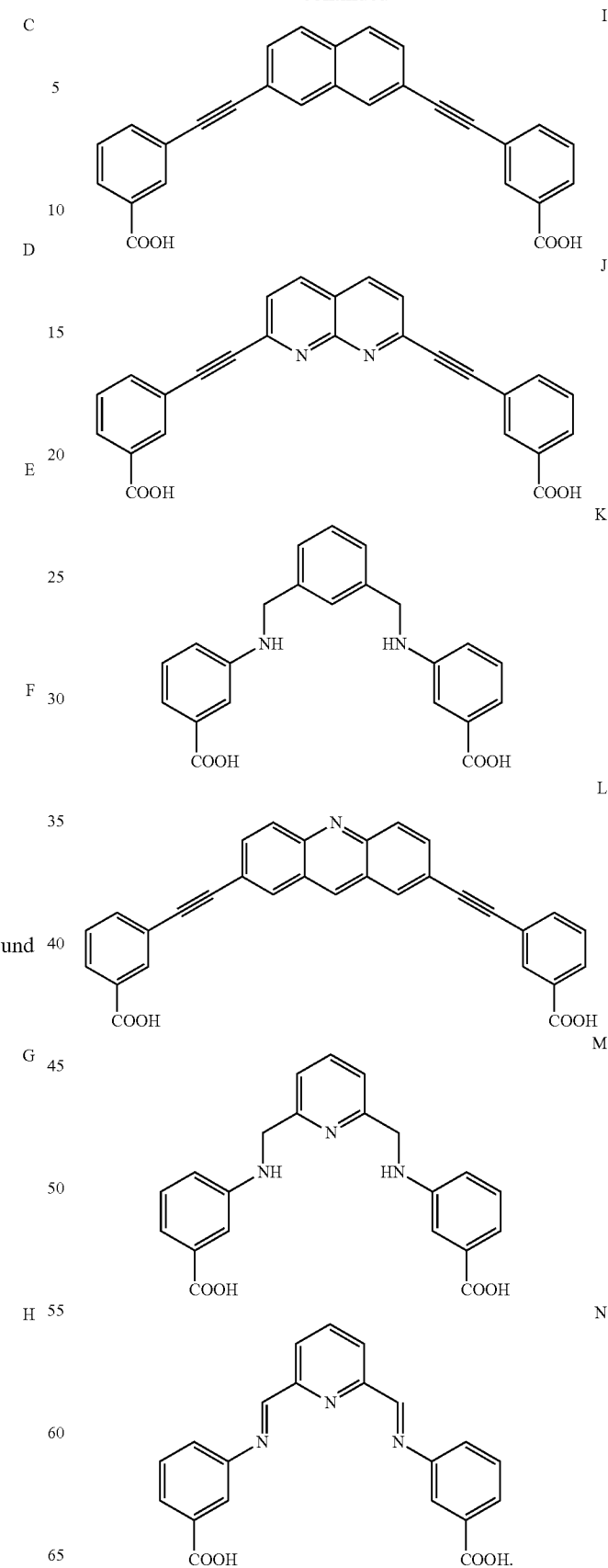

10. The porous material of claim 1, wherein the material comprises a plurality of pores, and wherein at least one pore comprises a single gas molecule.

11. The porous material of claim 10, wherein a majority of the plurality of pores each comprise a single gas molecule.

12. The porous material of claim 1, wherein the compound of formula (V) is selected from the following:

O
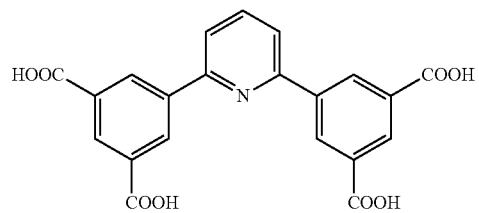

P
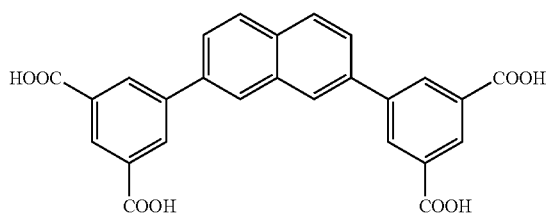

Q
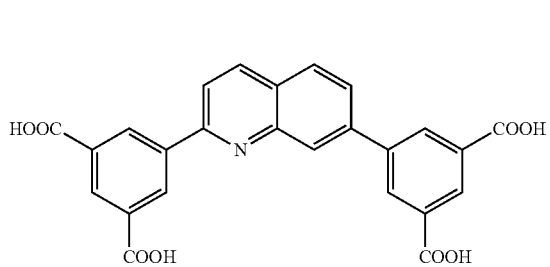

R
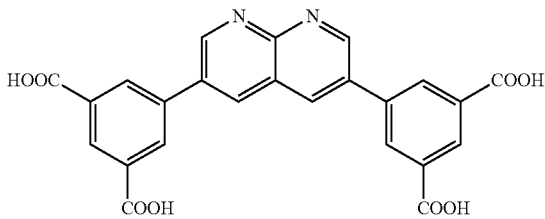

S
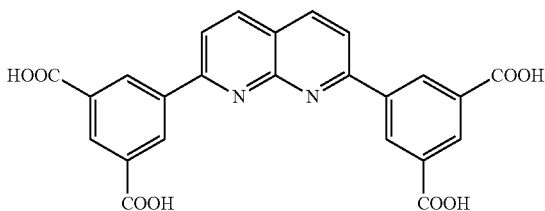

T
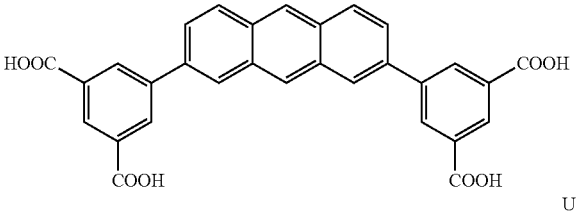

U
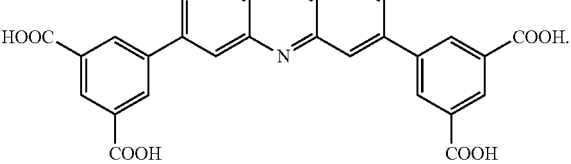

13. The porous material of claim 1, wherein the compound of formula (VI) is selected from the following:

V
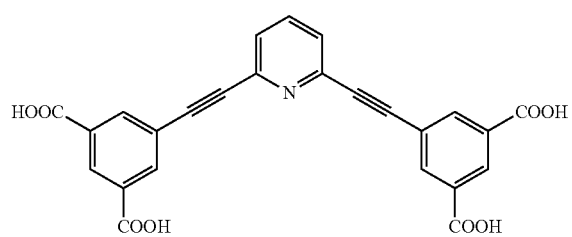

W
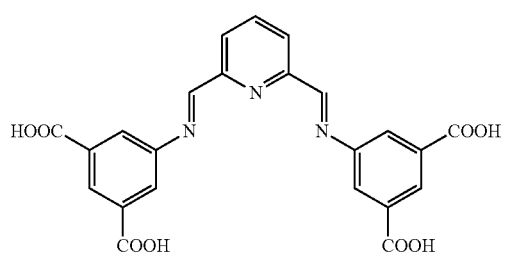

X
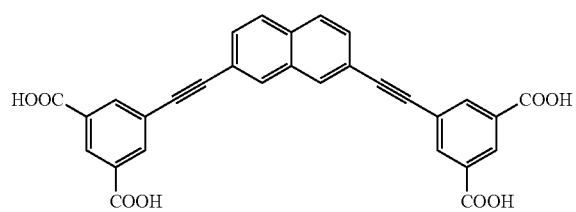

Y
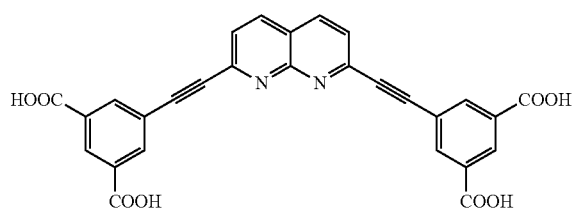

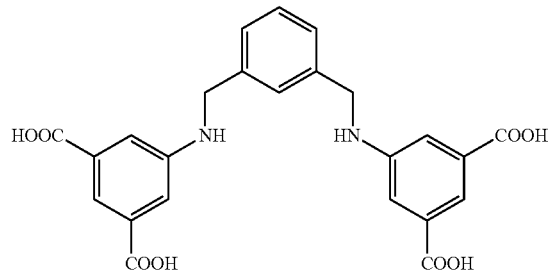
Z
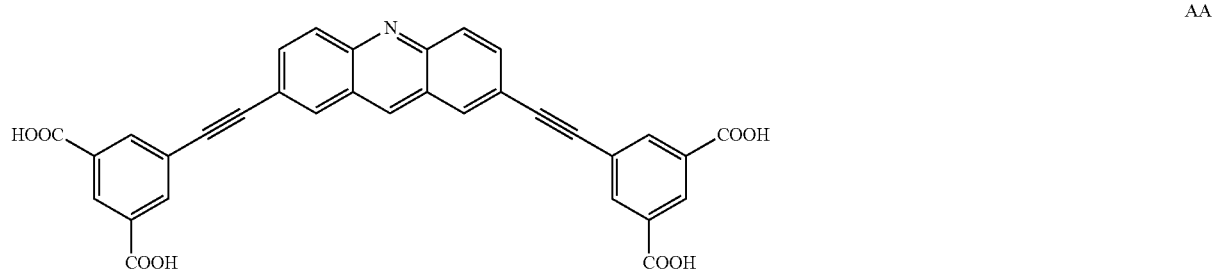
AA
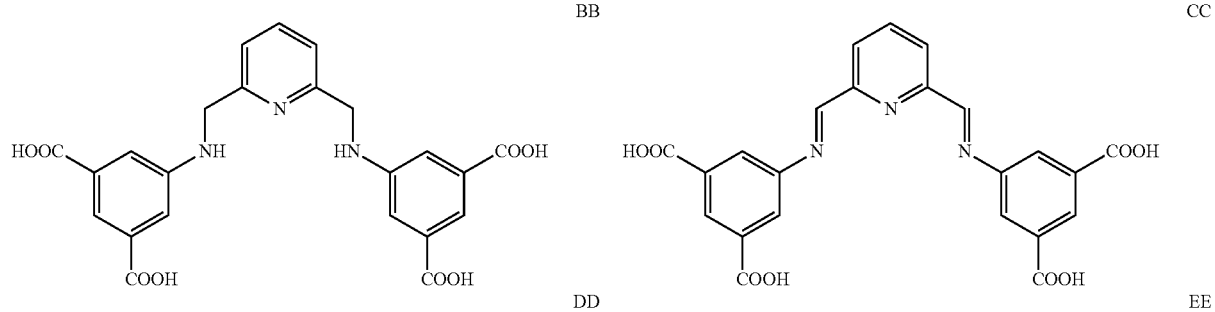
BB, CC
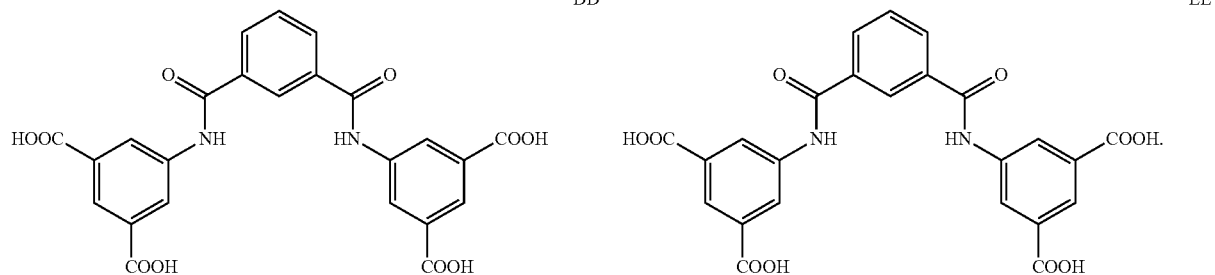
DD, EE
14. A method of binding a single gas molecule in a porous material, comprising contacting a porous material of claim 1 with a plurality of gas molecules, and the porous material selectively binds the single gas molecule.
15. The method of claim 14, wherein the plurality of gas molecules is further defined as a mixture of gas molecules,